United States Patent
Hooke et al.

(10) Patent No.: US 7,615,931 B2
(45) Date of Patent: Nov. 10, 2009

(54) PULSED DIELECTRIC BARRIER DISCHARGE

(75) Inventors: William McClure Hooke, Chapel Hill, NC (US); Allen Richard Martin, Sanford, NC (US); Mark Alan Ray, Raleigh, NC (US); Gary Elder McGuire, Chapel Hill, NC (US)

(73) Assignee: International Technology Center, Raleigh, NC (US)

( * ) Notice: Subject to any disclaimer, the term of this patent is extended or adjusted under 35 U.S.C. 154(b) by 945 days.

(21) Appl. No.: 11/120,153

(22) Filed: May 2, 2005

(65) Prior Publication Data

US 2006/0244386 A1 Nov. 2, 2006

(51) Int. Cl.
*H05B 31/26* (2006.01)
(52) U.S. Cl. .............. 315/111.21; 315/291; 118/723 E; 422/186.03; 427/569; 204/156
(58) Field of Classification Search ............ 422/186.03, 422/186.05; 427/569, 580; 204/156, 164, 204/170; 315/111.21, 291, 289, 360; 118/723 E
See application file for complete search history.

(56) References Cited

U.S. PATENT DOCUMENTS

| | | | |
|---|---|---|---|
| 3,432,663 A | 3/1969 | Anderson et al. |
| 3,824,400 A | 7/1974 | Lehovec |
| 4,230,994 A | 10/1980 | Bradley |
| 4,363,774 A | 12/1982 | Bennett |
| 5,508,590 A | 4/1996 | Sampayan et al. |
| 5,651,045 A | 7/1997 | Pouvesle et al. |
| 5,895,558 A | 4/1999 | Spence |

(Continued)

FOREIGN PATENT DOCUMENTS

WO   WO 2004/088708 A2   10/2004

(Continued)

OTHER PUBLICATIONS

Roth, et al., "The physics and phenomenology of One Atmosphere Uniform Glow Discharge Plasma (OAUGDP™) reactors for surface treatment applications", J. Phys. D: Appl. Phys. 38 (2005) 555-567, Feb. 3, 2005.

(Continued)

*Primary Examiner*—Haissa Philogene
(74) *Attorney, Agent, or Firm*—Miller Patent Services; Jerry A. Miller

(57) ABSTRACT

A dielectric barrier plasma discharge device consistent with certain embodiments of the present invention has a pair of electrodes spaced apart by an electrode gap. A dielectric is disposed between the electrodes. The electrode gap is provided with a gas at a specified pressure. A rapid rise time voltage pulse generator produces a voltage pulse across the electrodes to cause an extreme overvoltage condition, wherein the rapid rise time is less than a plasma generation time so that the extreme overvoltage condition occurs prior to current flow across the electrode gap. Due to the high voltages and high current densities, the product yields an extremely high instantaneous power density. This extreme overvoltage condition is also believed to lead to production of shock waves and runaway free electrons. The resulting plasma can be utilized to carry out many potential tasks including, but not limited to etching, deposition, and sterilization. This abstract is not to be considered limiting, since other embodiments may deviate from the features described in this abstract.

69 Claims, 11 Drawing Sheets

U.S. PATENT DOCUMENTS

| | | | |
|---|---|---|---|
| 6,059,935 | A | 5/2000 | Spence |
| 6,441,554 | B1 | 8/2002 | Nam et al. |
| 6,885,153 | B2 | 4/2005 | Quon |
| 6,924,608 | B2 * | 8/2005 | Czernichowski et al. .... 315/335 |
| 2002/0093294 | A1 | 7/2002 | Czernichowski et al. |
| 2003/0012718 | A1 | 1/2003 | Josephson et al. |
| 2004/0037736 | A1 | 2/2004 | Perruchot et al. |
| 2004/0045806 | A1 | 3/2004 | Neff et al. |
| 2004/0076543 | A1 | 4/2004 | Sokolowski et al. |
| 2004/0140194 | A1 | 7/2004 | Taylor, Jr. et al. |
| 2004/0183461 | A1 | 9/2004 | Kane et al. |
| 2005/0016456 | A1 * | 1/2005 | Taguchi et al. ........... 118/723 E |
| 2008/0106206 | A1 * | 5/2008 | Hooke et al. .......... 315/111.21 |

FOREIGN PATENT DOCUMENTS

WO     WO 2004/088708 A3     10/2004

OTHER PUBLICATIONS

Laroussi, et al., "Power consideration in the pulsed dielectric barrier discharge at atmospheric pressure", Journal of Applied Physics, vol. 96, No. 5, Sep. 1, 2004.

Bogdanov, et al., "Simulation of pulsed dielectric barrier discharge xenon excimer lamp", J. Phys. D: Appl. Phys. 37 (2004) 2987-2995, Oct. 8, 2004.

Golubovskii, et al., "Study of the homogeneous glow-like discharge in nitrogen at atmospheric pressure", J. Phys. D: Appl. Phys. 37 (2004) 1346-1356, Apr. 14, 2004.

APT13GP120BDF1 data sheet, Advanced Power Technology, Feb. 2004.

Grace, et al., "Plasma Treatment of Polymers", Journal of Dispersion Science and Technology, vol. 24, Nos. 3&4, pp. 305-341, 2003.

Lui, et al., "Electrical Modelling of homogeneous dielectric barrier discharges under an arbitrary excitation voltage", J. Phys. D: Appl. Phys. 36 (2003) 3144-3150, Nov. 25, 2003.

Chen, "Impedance Matching for One Atmosphere Uniform Glow Discharge Plasma (OAUGDP) Reactors", IEEE Trans. On Plasma Science, vol. 30, No. 5, Oct. 2002.

Mounir Laroussi, "Nonthermal Decontamination of Biological Media by Atmospheric-Pressure Plasmas: Review, Analysis and Prospects", IEEE Transactions on Plasma Science, vol. 30, No. 4, pp. 1409-1415, Aug. 2002.

Trompeter, et al., "Reduction of *Bacillus subtilis* and *Aspergillus niger* Spores Using Nonthermal Atmospheric Gas Discharges", IEEE Transactions on Plasma Science, vol. 30, No. 4, pp. 1416-1423, Aug. 2002.

Liu, et al., "Excitation of dielectric barrier discharges by unipolar submicrosecond square pulses", J. Phys. D: Appl. Phys. 34 (2001), 1632-1638, 2001.

Eimac Power Grid Tube—Quick Reference Data Sheet for 4PR60C/8252W, from Communication and Power Industries web site, Mar. 21, 1997.

International Search Report and Written Opinion, PCT/US06/15626; dated Aug. 28, 2007; Received Sep. 18, 2007.

A. J. Schwab and F. W. Hollinger, "Compact High-Power $N_2$ Laser: Circuit Theory and Design," IEEE Journal of Quantum Electronics, vol. 12, (1976).

J. Kohler, "Dielectric Barrier Discharge Pumped $N_2$ Laser," Applied Optics vol. 33 (1994).

G. Benedek, I. Boscolo, J. Handerek, S. Marchesini, C. DeMartinis, H. Riege, A. Scurati, "Displacement and Emission Currents From PLZT 8/65/35 and 4/95/5 Excited By A Negative Voltage Pulse at the Rear Electrode," Nuclear Instruments and Methods in Physics Research A, vol. 393, (1997).

M. Spaan, J. Leistikow, V. Schulz-von der Gathen and H. F. Dobele, "Dielectric Barrier Discharges with Steep Voltage Rise: Laser Absorption and Spectroscopy of NO Concentrations and Temperatures," Plasma Sources Science and Technology vol. 9 (2000).

J. Mankowski and M. Kristiansen, "A Review of Short Pulse Generator Technology," IEEE Transactions on Plasma Science vol. 28, (2000).

A. V. Azarov, S. V. Mitko, and V. N. Ochkin, "Xe Laser Pumped By Fast Electrons Generated in a Barrier Discharge," Quantum Electronics, vol. 32, (2002).

A. Khacef, J. M. Cormier and J. M. Pouvesle, "$No_x$ Remediation In Oxygen-rich Exhaust Gas Using Atmospheric Pressure Non-Thermal Plasma Generated By A Pulsed Nanosecond Dielectric Barrier Discharge," Journal of Physics D: Applied Physics 35 (2002).

U. Kogelschatz, "Dielectric-Barrier Discharges: Their History, Discharge Physics, and Industrial Applications," Plasma Chemistry and Plasma Processing, vol. 23 (2003).

A. V. Azarov, S. V. Mitko, and V. N. Ochkin, "An Open Barrier Discharge as Xe Laser Pumping Source," Advanced Lasers and Systems, Proceedings of SPIE vol. 5137, (2003).

K. Liu, Q. Hu, J. Qiu, and H. Xiao, "A High Repetition Rate Nanosecond Pulsed Power Supply for Nonthermal Plasma Generation," IEEE Transactions on Plasma Science, vol. 33, (2005).

* cited by examiner

PULSED DIELECTRIC BARRIER DISCHARGE

BACKGROUND

For many years, electric gas discharges have been used in a variety of applications including etching, deposition, sterilization, functionalization, etc. Commonly, these devices require sub-atmospheric pressures necessitating costly pressure locks and vacuum systems. Dielectric barrier discharge (DBD) systems, however, can operate at, below, or even above atmospheric pressure. Most DBD systems have been driven by continuous wave, radio frequency, power sources. In recent years, however, there has been increased use of pulsed power sources. In comparison with the RF DBD's, pulsed power DBD's, with their greater instantaneous powers, are able to achieve higher electron and reactive species densities together with higher electron energies leading to increased exposure dosage and decreased required processing time. In addition, the pulsed systems tend to be more stable and spatially uniform than the RF DBD's. Thus devices and techniques that lead to increases in power density without excessive gas heating, arcs, or narrow filamentary discharges are of considerable value. For reasons of economy we emphasize air or nitrogen as the working gases, although, glow-like discharges have been produced with this device in Nitrogen, Oxygen, sulfur hexafluoride ($SF_6$), carbon tetrafluoride $CF_4$), Helium, Neon, Argon, Krypton, acetylene, titanium tetrachloride ($TiCL_4$), and mixtures of some of the previously mentioned gases. The highest instantaneous power densities in nitrogen as in a glow-like DBD have been reported by Golubovskii (~2 kw/$cm^2$). The highest value observed using techniques described in this application is around 100 kW/$cm^2$.

As noted above, one useful application of plasma discharge systems is the use of the plasma for sterilization. U.S. patent application publication number US2004/0037736 A1 to Perruchot et al., which is hereby incorporated by reference, contains an extensive background treatment in the definition of sterilization and the various sterilization methods currently known and in use. As explained by Perruchot et al., the sterilization methods that use plasma discharge systems operate by creation of reactive species such as radicals of ionized and/or excited species. Various improvements on plasma discharge sterilization methods are further discussed in Perruchot.

BRIEF DESCRIPTION OF THE DRAWINGS

Certain illustrative embodiments of the present invention, which illustrate the method of operation, may be best understood by referring to the detailed descriptions that follow and the accompanying drawings in which.

DETAILED DESCRIPTION

Figure 1:
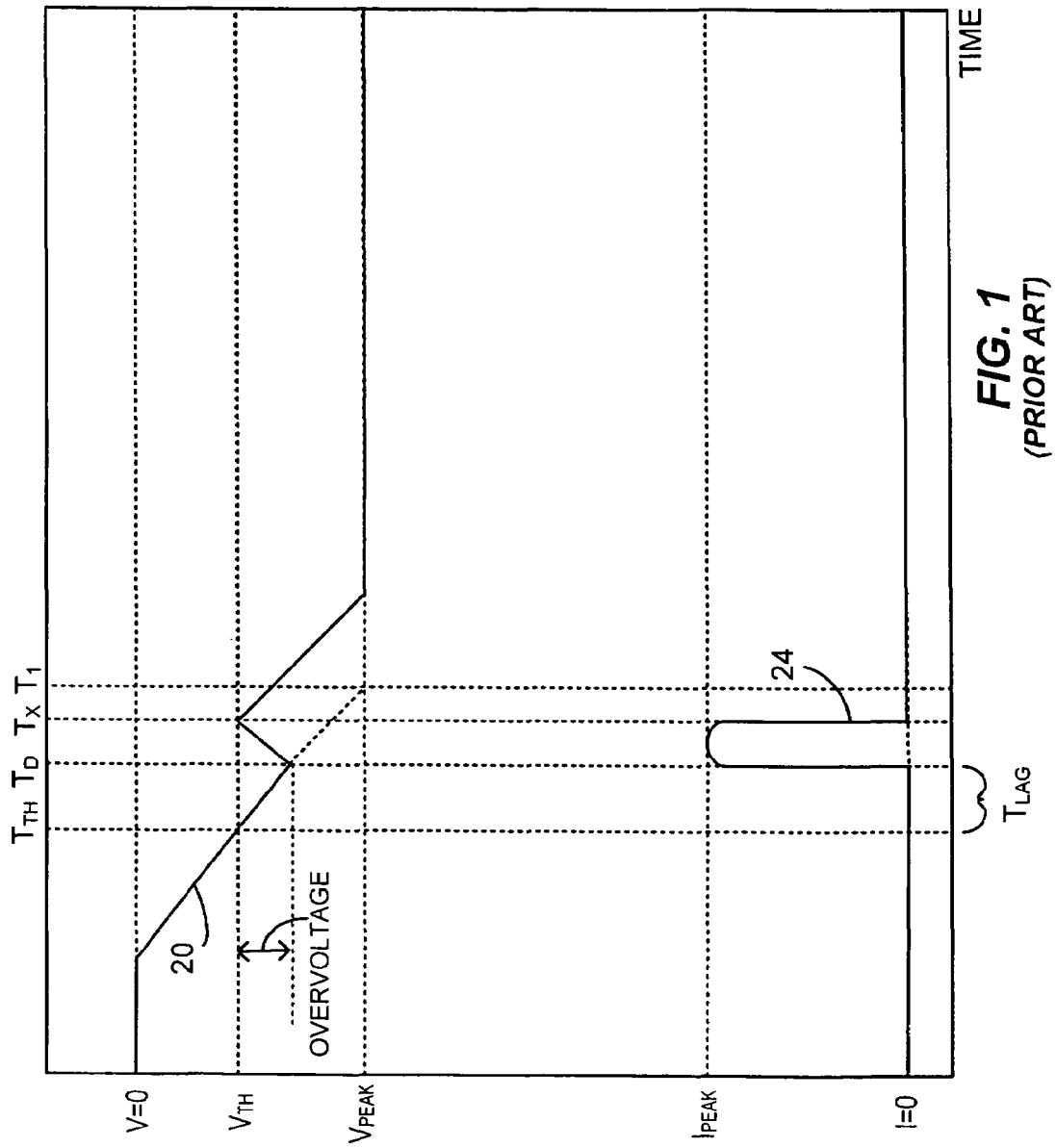
FIG. 1 is a somewhat idealized plot showing the leading edge of the voltage and current waveforms produced by a pulsed dielectric barrier gas discharge (DBGD) device with slow voltage rise times.

While this invention permits the detailed embodiment in many different forms, the drawings and descriptions shown here describe a specific embodiment, with the understanding that the present disclosure of this embodiment is to be considered as an example of the principles and not intended to limit the invention to the specific embodiment shown and described. In the description below, like reference numerals are used to describe the same, similar or corresponding parts in the several drawings. Much of the discussion to follow presents theory of operation that has not yet been fully proven as of this writing. Accordingly, the invention is not to be bound by such theories advanced.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearance of such phrases in various places throughout this specification is not necessarily referring to the same embodiment. Furthermore, the particular features, structures, or characteristics may be combined in any suitable manner in one or more embodiments without limitation.

It is emphasized that the present document discloses theory of operation as currently believed and understood. However, one skilled in the art will appreciate that systems, such as the prototype embodiment described herein, can be difficult to accurately characterize until numerous operating parameters are fully explored. Accordingly, the present disclosure offers the inventors' explanations of the physical phenomenon that have been observed, with such explanations being based upon the inventors' belief at the tine of this writing, but cautions the reader that the present invention is not to be bound by the theory disclosed herein as currently understood.

For purposes of this document, the following definitions will be used:

Threshold Voltage ($V_{TH}$)—the minimum voltage across the gap of a plasma generation device (glow discharge or glow-like discharge device) necessary to generate a plasma under a given pressure for a particular gas or gas mixture. This voltage varies depending upon the gas in the gap, size of the gap, gas pressure, electrode geometry and dielectric barrier characteristics.

Lag time ($T_{LAG}$)—the difference between the time the applied voltage across the gap reaches the threshold voltage ($V_{TH}$), and the time that current begins to flow in the gap.

Overvoltage—a condition in which a voltage much greater than $V_{TH}$ is rapidly applied across the gap of a plasma generation device. Overvoltage occurs during the Lag Time as described above and no current flows in the gap. A small incidental overvoltage may occur in pulsed plasma generation devices but this has a small effect unless the applied voltage is very high and the rise time is short compared to the Lag Time ($T_{LAG}$).

Extreme Overvoltage—a condition wherein a high level of overvoltage is established—generally speaking, this condition begins to manifest itself when the peak pulse voltage is greater than about 2 times the threshold voltage $V_{TH}$. It is believed that extreme overvoltage effects may be observable as low as approximately 1.5 times the threshold voltage for discharges. Such extreme overvoltage conditions are possible by using an extremely rapid rise time voltage generator that is able to achieve an extreme overvoltage condition during the lag time ($T_{LAG}$) preceding the breakdown.

Dielectric Barrier Discharge (DBD) or Dielectric Barrier Glow Discharge (DBGD)—interchangeable terms used to refer to a plasma discharge device, method or event wherein a dielectric barrier is placed between the electrodes of a plasma generation device.

Filamentary Discharge or Filaments—These terms are used to describe a discharge which has regions of high current density, typically >100 microns in diameter, with little or no discharge in the area between the filaments. This discharge is very non-uniform across the surface of the gap and is typical of many AC discharges.

Pulsed Plasma System or Pulsed DBD or Pulsed DBGD—a plasma generation device driven by a pulsed drive signal (as contrasted to a DC or AC (e.g., sinusoidal or RF) drive signal).

Electrode Gap or Plate Gap or simply Gap—the gap between the electrodes of a plasma generation device. A dielectric is generally interposed in the gap to prevent arcing in dielectric barrier discharge systems.

Runaway electrons: electrons which are continuously accelerated across the gap or some portion of the gap. Electrons in a discharge may undergo inelastic collisions with atoms and molecules which create ions and radicals. As the electron energy increases, the probability of collision with a gas atom decreases. At sufficiently high overvoltages, the electron energy may increase, between collisions, more than the energy that is lost when a collision occurs. Except for the collisions the electron energy continually increases as the electron accelerates in the gap or some portion of the gap (e.g., prior to a collision). This may produce electrons with up to greater than a keV of energy.

Planar Electrode—an electrode can be considered planar as opposed to a point if the electrode gap is much less than the radius of curvature of the point of the electrode.

Gas is used herein to mean either a mixture of gasses including mixtures such air, as well as a substantially pure gas such as nitrogen.

Current Spike, Initial Spike or Spike Region—the initial spike of current produced in the discharge across the gap of certain embodiments consistent with the present invention; a region of operation of a glow or glow-like discharge according to certain embodiments consistent with the present invention.

Current Pedestal, Pedestal, or Pedestal Region—a secondary surge or flow of current following the current spike produced in the discharge across the gap of certain embodiments of the present invention; a region of operation of a glow or glow-like discharge according to certain embodiments consistent with the present invention.

Plasma Generation Time—the time from the beginning of application of voltage across the gap until the time of discharge in a pulsed plasma generation system.

Sustaining Voltage—the voltage regulating properties of gas discharges. The sustaining voltage is the voltage that the discharge will fall to once breakdown has occurred.

Glow Discharge—This term, as used herein, is intended to mean both glow discharge phenomenon and glow-like discharges both of which are characterized by a uniform glow between the electrodes as opposed to spark or filamentary discharges.

Discharge—The term is used interchangeably with glow discharge, glow-like discharge, plasma discharge, or plasma.

Object or Object of Matter—This term is intended not only to embrace solid objects but also fluids, gasses, liquids, semi-solids and materials in any state of matter. Thus, for example, reference to placing an object within a plasma can be interpreted to mean the same thing as exposing a liquid or gas to the plasma.

Turning now to FIG. 1, it is instructive to view an illustration of the leading edge of the voltage and current pulses of a conventional pulsed DBD system in order to appreciate the distinctions associated with embodiments consistent with the present invention. In FIG. 1, a voltage pulse 20 (shown greatly exaggerated in time so that the rise time is apparent) is applied to a pair of electrodes which have a dielectric barrier disposed between in a conventional manner. A negative-going voltage pulse is illustrated to correlate with the measurements used in tests conducted on prototypes of certain embodiments of the present invention. In this representation, a discharge occurs between the electrodes starting at time $T_D$ which interrupts the voltage waveform. The time difference between the time $T_{TH}$ the voltage reaches $V_{TH}$ and $T_D$ is referred to herein as the lag time $T_{LAG}$ as defined above. At time $T_D$, current begins to flow, as illustrated by the pulse in the current curve 24, thus establishing a brief glow discharge between the electrodes, until approximately time $T_X$. Also at time TX, the voltage reaches its maximum sag as a result of the current pulse. The discharge has a peak power density that is a function of the product of the threshold voltage $V_{TH}$ and the peak current $I_{PEAK}$. In this illustration, the applied voltage drops during the current pulse as the voltage across the dielectric barrier increases. Had a discharge not occurred, the peak voltage would have been achieved at time $T_1$.

In conventional DBD devices and systems, the voltage pulse is established such that the peak voltage $V_{PEAK}$ is slightly greater than the threshold voltage $V_{TH}$ required to establish the glow discharge. Increasing the voltage beyond this threshold may have no noticeable effect upon the operation of the DBD device since the increased voltage will simply charge the dielectric barrier and terminate the discharge. As can be seen in FIG. 1, a small overvoltage may occur when using a slow rise time, but this is a small percentage of the pulse amplitude due to the slow rise time. Increasing the applied voltage much beyond the threshold voltage $V_{TH}$ is generally considered to be of little value. This will be true using conventional pulse generators with relatively slow rise times relative to the lag time as illustrated (and exaggerated for clarity in explanation) in FIG. 1.

One of the problems that have conventionally faced those attempting to generate plasmas using pulse generators has been that it is somewhat difficult to generate the high pulse voltages required to break down the gap. To simplify the process, the gasses placed in the electrode gap are often gasses that more easily breakdown such as Argon or Helium or mixtures thereof. Additionally, to make it even easier to create the discharge, such gasses are often used at lower than atmospheric pressure. Such expedients have also often worked to reduce the lag time ($T_{LAG}$) between reaching the threshold voltage ($V_{TH}$) and the occurrence of a discharge. In many cases, this leads to near total elimination of the lag time, and the discharge occurs immediately when the voltage across the gap reaches $V_{TH}$.

Therefore, with a low pressure and relatively low breakdown voltage gas, the time lag combined with the rise time has been such that the effect of overvoltage has been entirely unexplored. DBGD systems have evolved in a manner that even if a scenario were created which caused an overvoltage condition, the level of overvoltage is somewhat self-limiting. Consider for example the overvoltage shown in FIG. 1. This overvoltage represents an extension of the rise time of pulse 20 for the duration of the lag time ($T_{LAG}$). This would create only a small overvoltage condition that has an insignificant effect on the plasma generated.

Thus, as DBGD systems have evolved, the conventional ways of thinking about how to create a discharge have had a great influence on the progress in this field. As atmospheric glow discharge systems were developed, the designs have gravitated toward the use of more easily ionized gasses to relieve engineering problems associated with higher pressure devices. Many of these features naturally inhibited exploration of operational zones involving overvoltage such as those explored in conjunction with embodiments consistent with the present invention. Moreover, the difficulty in obtaining the rapid rise times and extreme voltages and currents to effect the necessary overvoltage condition has left this space unexplored.

In accordance with certain prototype embodiments consistent with the present invention, a DBD system, operating at either reduced pressure or at atmospheric pressures and driven by a high voltage, short rise time pulsed power supply, has been made that significantly exceeds the performance of known DBD systems found in the literature. The fast rise voltage pulse creates two distinct discharge regions which are referred to herein as the spike region followed by the pedestal region, as defined above. This prototype system has been shown to deliver significantly more instantaneous power (on the order of one MW) than other known DBD devices. Also the additional power and total energy delivered during the pedestal current region are without known precedent. The rapid rise time is used to create an extreme overvoltage, which is the difference between the DC breakdown voltage for a specific gap distance and pressure, and the actual applied peak voltage at the time breakdown occurs. It takes a finite amount of time to breakdown the gas once the DC breakdown voltage is exceeded. For fast rise times, the overvoltage can be several times the DC breakdown voltage. This overvoltage condition is reached prior to the breakdown resulting in high levels of instantaneous power and other potentially desirable attributes as will be discussed herein.

Figure 2:
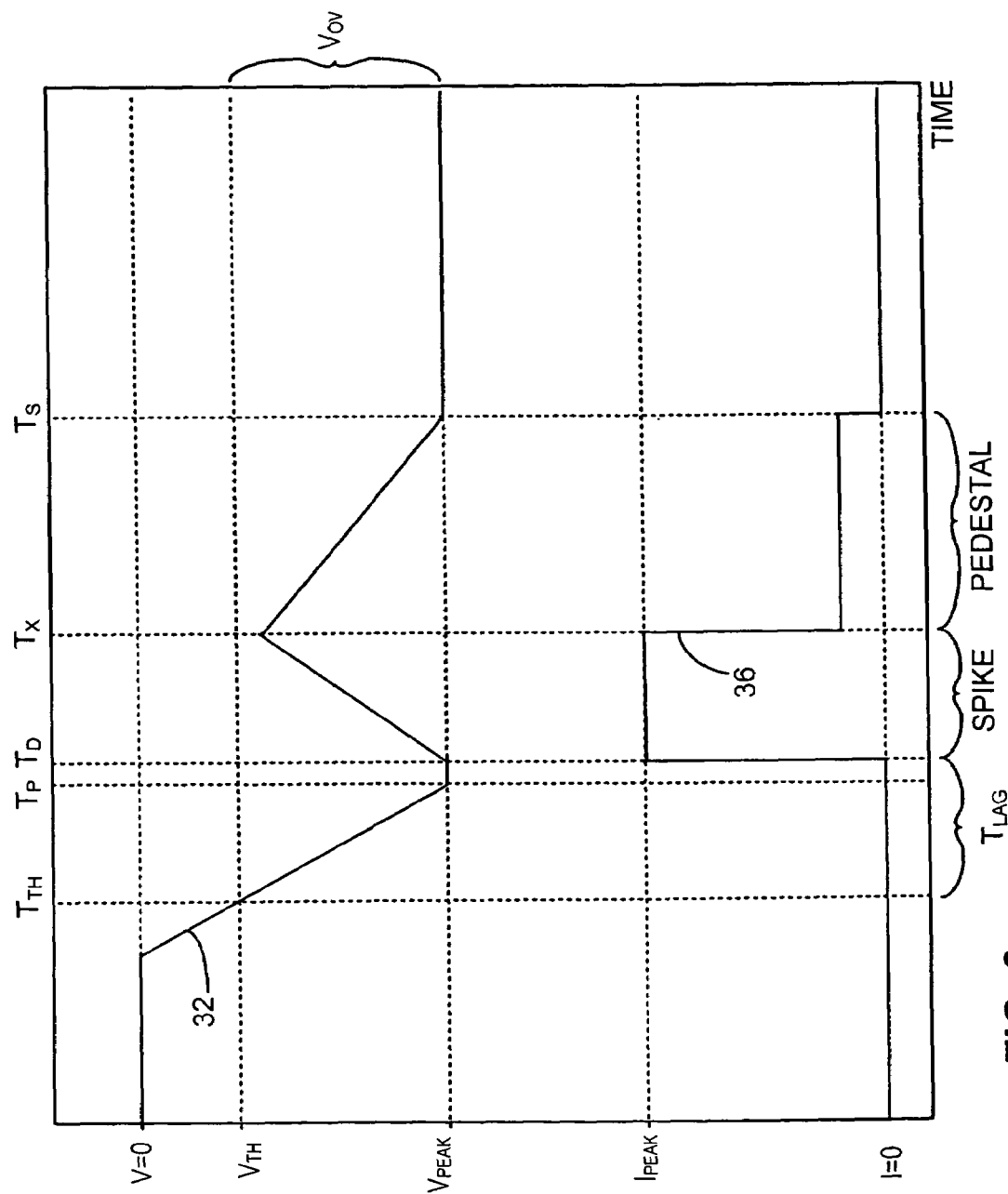
FIG. 2 is a somewhat idealized plot showing the leading edge of the voltage and current waveforms produced by a pulsed DBGD device consistent with certain embodiments of the present invention.

Referring now to FIG. 2, a somewhat idealized set of voltage and current curves (at the pulse's leading edge) for an embodiment consistent with the present invention is depicted (exaggerated rise times and operational regions). Whereas the conventional DBGD systems utilize easy-to-discharge gasses, FIG. 2 illustrates some of the phenomenon which occur when more difficult-to-discharge gasses are explored, although the present system is capable of operating with a wide variety of gases including the easy-to-discharge gases, using a pulse generator capable of much more rapid rise times relative to the Lag-Time than those conventionally used for this purpose. It should be noted that there is no scale associated with either FIG. 1 or FIG. 2. For purposes of this discussion, these drawings are only intended to illustrate the differences that can be obtained by using extreme overvoltage and rapid rise times.

In FIG. 2, voltage pulse 32 is applied to the electrode gap with a rapid rise time such that the threshold voltage $V_{TH}$ is reached at time $T_{TH}$ and dramatically exceeded prior to discharge time $T_D$. For purposes of discussion, a peak voltage is reached at time $T_P$ which is just prior to the time of discharge $T_D$. In this example, the peak value of the pulse $V_{PEAK}$ is shown to be approximately triple the threshold voltage $V_{TH}$, resulting in an "extreme overvoltage" condition as defined above. Generally speaking, in experiments to date, the interesting effects of overvoltage begin to manifest themselves when the peak voltage $V_P$ is about double the threshold voltage. Peak voltages $V_P$ of approximately triple the threshold voltage have been used experimentally, and even greater voltages are expected to produce even more dramatic results. Interesting effects may begin to manifest themselves at lower extreme overvoltage conditions (e.g., 1.5 times or 1.75 times the threshold voltage), but generally speaking, higher levels of extreme overvoltage generate more instantaneous power, and are thus potentially more useful. Additionally, in some instances achieving the extreme overvoltage condition may be easier when gasses that are conventionally harder to break down are used.

In this illustration, it is noted that the rise time to achieve peak voltage of the voltage pulse 32 is shorter than the lag time $T_{LAG}$ between the pulse 32 crossing the threshold voltage $V_{TH}$ and the beginning of the current flow as shown by current curve 36. This permits the voltage pulse to continue to increase in value to its peak prior to the discharge at time $T_D$. Commonly, the peak voltage is generated by switching a charged capacitor across the gap. As the initial current spike is drawn from this capacitor, the gap voltage sags to approximately the gap threshold voltage. The applied voltage sags to the sum of the threshold voltage and the dielectric capacitor voltage as shown.

The initial spike region is between approximately $T_D$ and $T_X$ in FIG. 2. Following this initial spike, a pedestal region develops where current continues to flow after the initial spike and contributes substantially to the power generated. This pedestal region contains substantial energy, thus increasing the overall energy and the average power created in the discharge. The pedestal region extends from approximately $T_X$ to approximately $T_S$. The source of current for the pedestal region is apparent since the voltage waveform is seen to ramp linearly from $V_{TH}$ to $V_{PEAK}$ during this time. This voltage ramp is charging the dielectric capacitor to the peak applied voltage through the gap thereby producing the current pedestal. In certain experiments, the energy in the pedestal region has been measured to be approximately 50% of the energy delivered in the spike region, thus substantially increasing the overall energy. The approximate 50% number should not be considered limiting in any way since this percentage will vary greatly as the variable operating parameters and circuit parameters are varied.

It can be shown that the extreme overvoltage condition created by the application of substantially higher voltage prior to discharge causes breakdown to occur, and an initial spike of current to flow, at a time when the gap voltage is considerably higher than the breakdown voltage. There may be several beneficial aspects to the extreme overvoltage in certain embodiments (but no assertion is made that any or all such benefits are obtained in all embodiments consistent with the present invention). Due to the high voltages and high current densities, the product yields an extremely high instantaneous power density which greatly exceeds the power densities in known DBGD systems. Due to the pulsed nature of the discharge the gas temperature remains low with little average temperature increase, in experiments run to date.

By way of example, in experiments using the prototype system, a sheet of ordinary writing paper placed in the plasma does not exhibit discolorations with the unaided eye that might be expected from another plasma system. The gas temperature depends upon the specific operating conditions of the system such as the pulse frequency, power density, gas pressure among other things so that the average gas temperature could rise under certain operating conditions The average energy of the gas is more than 1 order of magnitude less than the average energy of the electrons. A fraction of the electrons generated in the plasma are very energetic and may be utilized as a means to cause rapid heating of surfaces under appropriate conditions. The energetic electrons are believed to be a result of the, overvoltage which provides the accelerating potential to generate the high energy electrons in the discharge, i.e., a runaway electron condition is believed to exist in the spike region.

The runaway electrons may be used in a beneficial manner for certain applications. No runaway electrons are believed to be produced in the pedestal region in experiments to date since it is believed that the gap voltage cannot be greater than the breakdown (or sustaining) voltage of the gap. In another potentially beneficial aspect, a theoretical analysis of the discharge indicates that a shock wave is created in the gas at each pulse from the pulsed voltage source. By way of inference, particles placed in a tray and exposed to the discharge are displaced; the extensive displacement of the particles is believed to be a result of the shock wave. This shock wave may be advantageously utilized for certain applications. For example, the shock wave has been observed to agitate small particles placed in the plasma. Such agitation could possibly be useful, for example, in functionalization processes to prevent the small particles from becoming agglomerated, and may facilitate more even exposure of the particles to the plasma. Again, however, it is emphasized that the actual presence of shock waves and runaway electrons are presently theorized, and that the present invention should not be limited by the current understanding of the theory of operation of the experimental prototype.

In certain embodiments consistent with the present invention, a custom designed rapid rise time pulse generator was developed in order to achieve the high voltages and currents needed to produce the desired overvoltage condition. This custom designed pulse generator, at this writing, was capable of generating voltage pulses in excess of 27 kV with a rise time of 100-350 ns. The overall plasma generation system has instantaneously generated power in the range of 800 kW to 1 MW for about 20 nS, and has produced pedestal current with power and duration on the order of 24 kW and 300 nS. This is approximately triple the voltage and five times the current of the nearest known systems at this writing. The resulting instantaneous power density is correspondingly greater. Since this power density is so much higher than other discharges described in the literature, the density of charged particles is estimated to be 1-2 orders of magnitude greater than that of other previously reported dielectric barrier discharges.

In one embodiment, the system is driven by a high voltage pulse generator which uses a switch tube to switch high voltage onto a variable parallel capacitance (in parallel with any stray capacitance), a pulse sharpener (pulse shaper), and finally the DBD system, as will be described later. It is noted that the prototype system operated without benefit of the pulse sharpener, but it is believed that use of such pulse sharpener will further enhance operation. The prototype system used for experiments described herein has two parallel plates, between which materials may be placed for etching, deposition, sterilization, functionalization, etc.

Various gases may be introduced at a controlled flow rate around the electrodes or through them by means of small holes in the plates or in a chamber surrounding the parallel plates. The parallel plates have at least one side covered with a dielectric that will withstand the applied voltage. Alumnia, boron nitride (BN), glass, and polyimide films such as DuPont Kapton® have been utilized in tests and proven to be hardy enough to withstand the high voltage pulsing. The best dielectric identified to date has been alumina. Higher dielectric constant materials could be used, providing they can withstand the applied voltage. A higher dielectric material is desirable because it would increase the capacitance, which in turn would store more charge and provide increased discharge duration.

Figure 3:
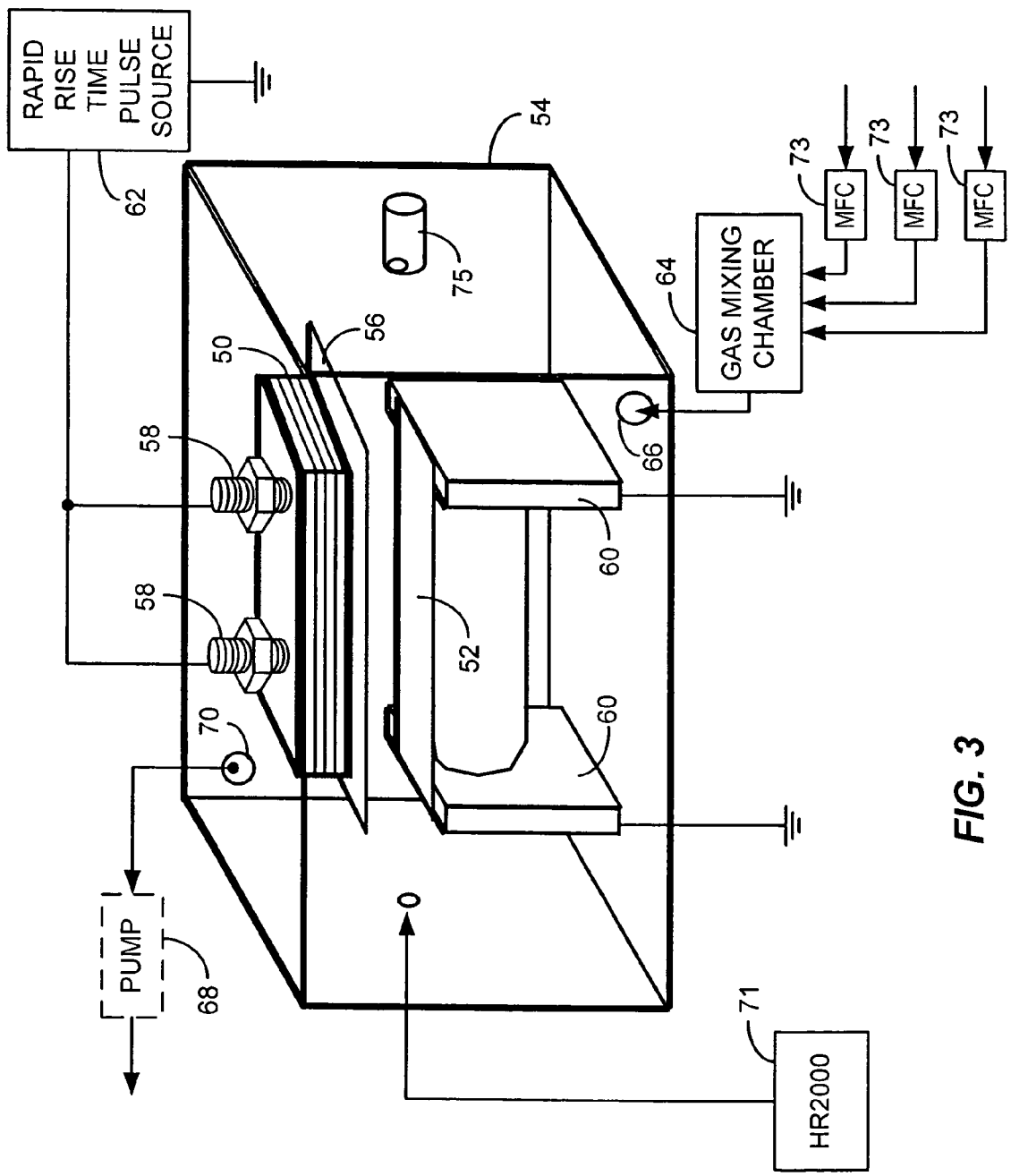
FIG. 3 is an illustration of a fixture used in the development of a DBGD consistent with certain embodiments of the present invention.

In carrying out the experiments to be described, the basic test setup shown in FIG. 3 was used. In this setup, the two electrodes 50 and 52 are mounted within a chamber 54. The top electrode 50 is mounted to the upper surface of the chamber 54 with threaded studs and nuts 58. The gap can be adjusted for various experiments using the threaded studs, by shimming or otherwise adjusting the position of the top electrode plate 50 in relation to the bottom electrode 52. Gaps ranging from less than 1 mm to 8 mm have been used in experiments. The dielectric barrier 56 in this fixture is a 0.025 inch (0.635 mm) thick 4.0×4.0 inch (10.16 cm×10.16 cm) Alumina ($Al_2O_3$) plate attached to the electrode 50. The electrode as shown is rectangular, but in certain cases a circular plate, e.g., a 1.125 inch (2.858 cm) diameter plate, was used. Also, although only the upper electrode included a dielectric barrier, other arrangements such as a dielectric barrier on the bottom electrode or both electrodes have been used.

The lower electrode 52 is mounted in a rigid configuration to thermally conductive blocks that can be used to connect the lower electrode 52 to the pulse generator (or make a ground connection as shown). As originally developed, large amounts of heat were anticipated, and certain provisions were made in the fixture to provide for liquid cooling. However, the plasma generated has been quite cool, removing the need to cool the electrodes in experiments conducted to date.

In this illustration, a rapid rise time pulse generator 62 is coupled to the upper electrode and ground such that the pulses are applied across the electrode plates 50 and 52 of the fixture. Gasses can be introduced and mixed in a gas mixing chamber 64 and delivered to the interior of the fixture via port 66. The gas mixture can be vented or pumped out using pump 68 through port 70. Experiments have been successfully conducted with internal chamber pressures ranging from approximately 300 Torr to approximately 1100 Torr. It is anticipated that the present arrangement could also operate at higher and lower pressures.

For the test setup, an Ocean Optics Spectrophotometer (model HR 2000) was used as an emission spectrometer to detect the species present in the plasma by resolving the plasma emission spectrum from about 200 to 1100 nm in wavelength. Mass Flow Controllers 73 or other devices can be used to control the flow of gasses into the mixing chambers. In present experiments Mass Flow Meters were used to control and limit the flow of gases since the system was operated at atmospheric pressures. A port 75 is provided in the test fixture for a photodiode or other device for measuring or monitoring the optical intensity.

Figure 4:
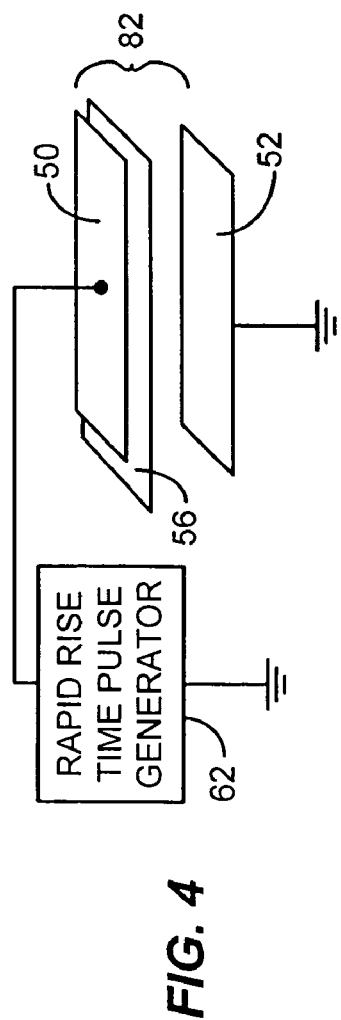
FIG. 4 is a block diagram of a DBGD device consistent with certain embodiments of the present invention.

Referring now to FIG. 4, a simplified schematic block diagram of the first embodiment of a glow discharge device is depicted. In this embodiment, the first electrode 50 has an attached dielectric barrier 56. A second electrode 52 is located below the dielectric barrier. The electrodes are separated by a gap 82. The rapid rise time pulse generator 62 is used to apply the extreme overvoltage condition to the electrodes 50 and 52 as previously described. The gap is the space between the dielectric and the lower electrode.

Figure 5:
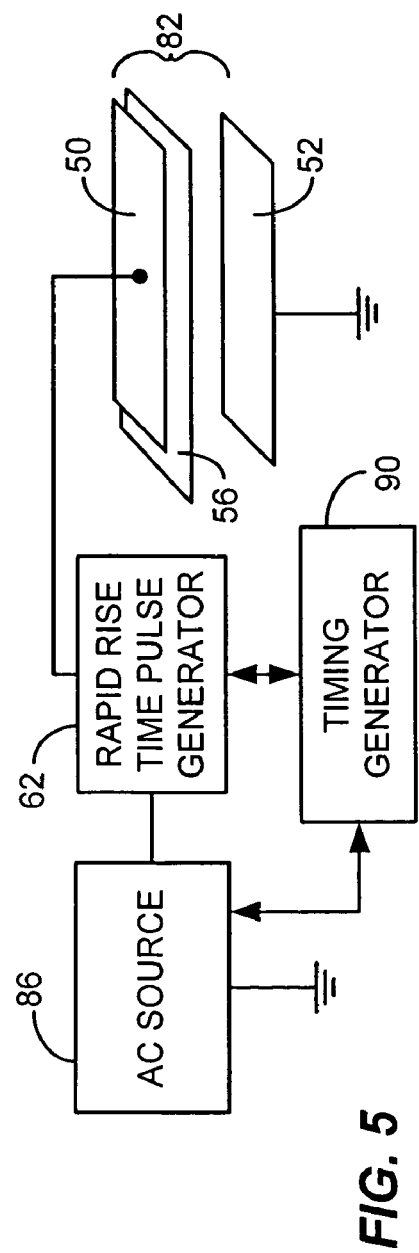
FIG. 5 is a block diagram of another embodiment of DBGD device consistent with certain other embodiments of the present invention.

Referring now to FIG. 5, an alternative embodiment is shown. By combining a low frequency RF voltage with the pulsing system, a higher extreme overvoltage condition can potentially be achieved than with the pulsing system alone. In this embodiment the phase of the pulse, relative to the RF voltage, can be controlled with a sensing and control circuit so that the pulse may be positioned at any point on the RF waveform. The combination of AC and pulsed operation raises the baseline of the pulse so that the overvoltage is increased by the amplitude of the applied RF voltage. The rapid rise time pulse generator 62 of this embodiment is used in conjunction with an AC or RF source 86 (sinusoidal, square wave, pulsed or any other suitable alternating current waveform) to apply the extreme overvoltage condition to the electrodes 50 and 52 as previously described. In this embodiment the use of the AC source 86 again is used to further increase the degree of extreme overvoltage condition appearing across the gap 82. Timing may be controlled using any suitable mechanism which derives timing for the pulses from the AC source 86.

In yet another embodiment not shown, a hybrid arrangement may be provided in which a DC offset in conjunction with an AC source and the pulse generator 62 are combined in a manner which further maximizes the extreme overvoltage condition.

Figure 6:
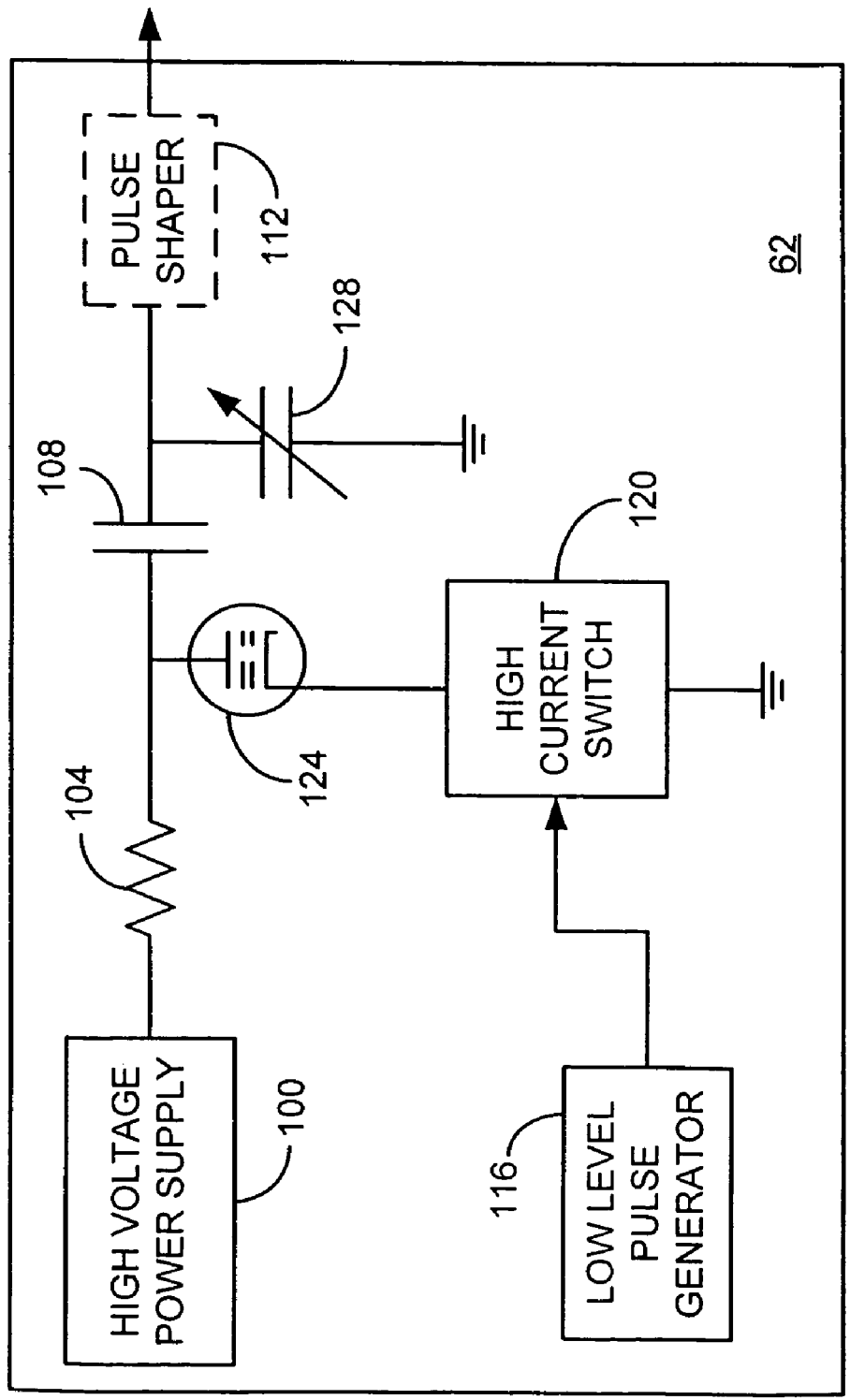
FIG. 6 is a diagram of the pulse generator 62 consistent with certain embodiments of the present invention.

FIG. 6 depicts a rapid rise tine pulse generator 62 in accordance with certain embodiments of the present invention. In this embodiment, a commercial or custom designed high voltage power supply 100 is provided which produces, for example, greater than 15 KV. In the prototype embodiment, a commercial 30 kV supply was utilized. The limit of 27 kV is the maximum voltage that the switch tube was conditioned to withstand. The output of the high voltage power supply is connected to a resistor 104 (e.g., 30 K ohms, 300 Watts) in series with a capacitor 108 (e.g., 0.025 µF, 30 KV). The switch tube 124 will switch the voltage on the high voltage side of capacitor 108 to ground which, in turn, reflects a negative going high voltage pulse to the output. This output is shown passing through a pulse shaper (pulse sharpener) circuit 112 (e.g., a winding on a saturable torroidal core with a bias winding used to reset the core between pulses.) which further decreases the rise time.

A low level pulse generator circuit 116 is used to control a high current switch circuit 120. The high current switch circuit grounds the cathode of a high current switch tube 124 thereby biasing the tube in a conducting state. The vacuum tube is a high voltage, high current switch tube such as an industry standard type 4PR60C (Y543) pulse tetrode vacuum tube, available from Communications and Power Industries (such as those manufactured by Eimac). The high current switch circuit is realized in the prototype using high voltage IGBT switching transistors such as industry standard number APT13GP120BDF1, commercially available from Advanced Power Technology. An adjustable or fixed capacitor 128 can also be used in parallel with the output, preceding the pulse shaper 112, in accordance with certain embodiments.

The switch tube 124 provides an initial fast rise time for the pulse and the pulse shaper refines the pulse to decrease the rise time and thereby increase the overvoltage condition. The parallel capacitance 128 (plus stray capacitance such as the plate to screen capacitance of switch tube 124) provides the initial current spike. The parallel capacitance is tunable so that the charge available for the spike can be varied depending on the application. A current transformer and high voltage probe (not shown) were used on the pulse circuit output to provide the data for the I-V curves shown later. The dielectric barrier 56 used in the experiments to be described is a 0.025 in. thick plate of high purity alumina which covers one of the electrodes (e.g., 50). A single dielectric barrier or a dielectric barrier on each electrode may be used with similar effect. The electrode area may range from as small as 1 square centimeter to several hundred square centimeters or more. The discharge characteristics as exemplified in the following traces will scale with electrode area, so long as the power supply capacity is scaled to compensate for larger electrode area. The scale factor of power with area is approximately linear.

Figure 7:
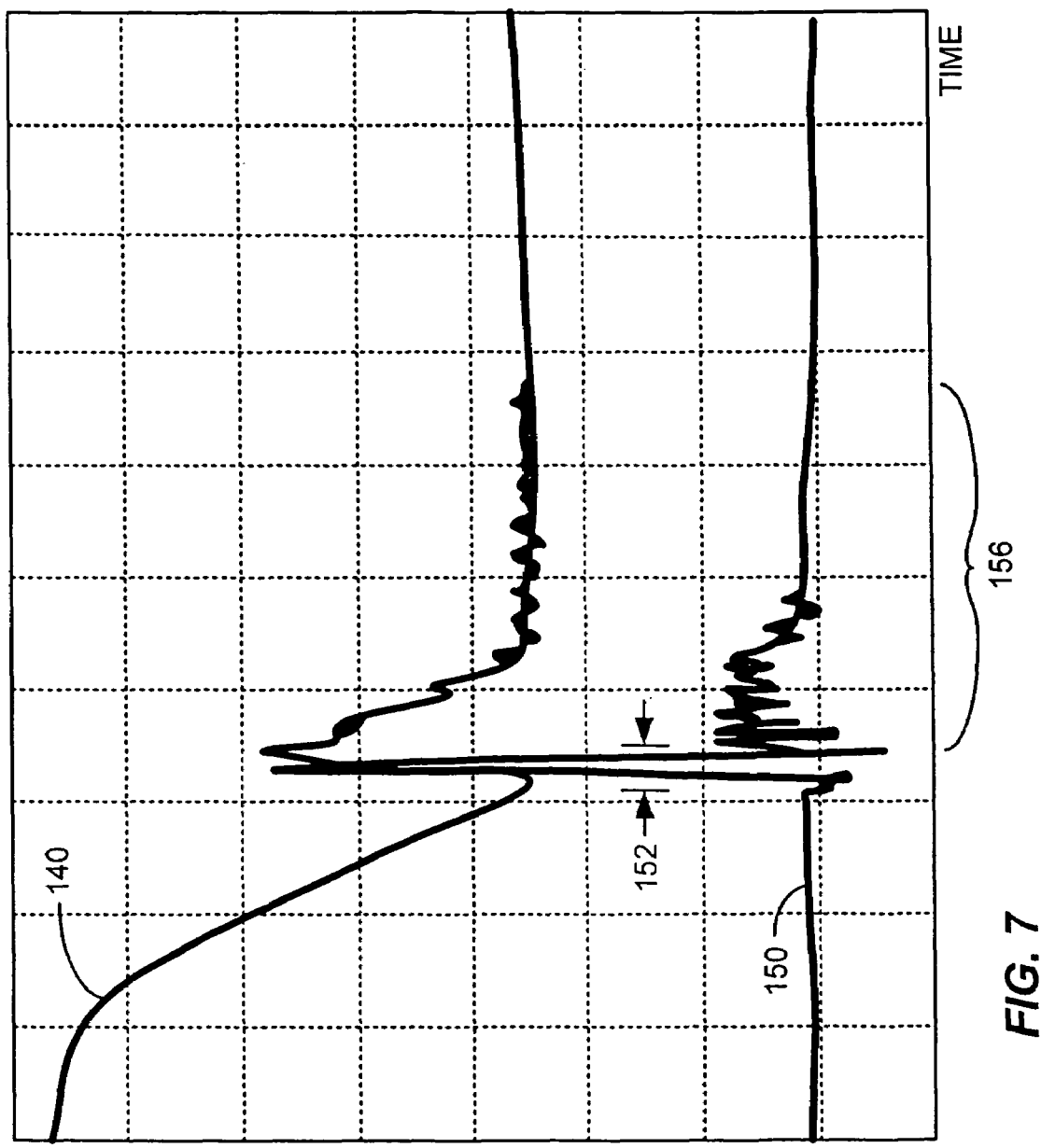
FIG. 7 is an example of the leading edge of the voltage and current waveforms using the system and methods consistent with certain embodiments of the present invention.

FIG. 7 and all traces subsequent thereto are drawings generated by reference to photographic images of actual test traces. Accordingly, they should be viewed as approximations of the actual test data. Evidence of the increased plasma power is shown in the reproduction of voltage and current traces shown in FIGS. 7-8. During these experiments, the gas used was nitrogen, the gap between the electrodes was 3.5 mm, and the dielectric was a 0.025 in thick 4.5 in×4.5 in $Al_2O_3$ plate attached to the top 1.125 in diameter circular electrode.

FIG. 7 shows a reproduction of a voltage trace 140 and a current trace 150 as obtained from actual experimental data. In this graph, the voltage scale is 5 KV/division, the current scale is 10.0 Amp/division and the sweep speed is 250 ns/division. The spike region 152 of the current pulse represents an initial spike of current through the gap during the initial part of the discharge. The spike region begins after the pulse voltage has reached its maximum value (at the end of the pulse generation time) and the end of the lag time. The pedestal region 156 begins immediately following the spike region. The widths of spike region 152 and pedestal region 156 should not be viewed as absolute from these drawings, since the drawings are illustrations of the actual voltage traces and since the actual beginning and end of such regions is difficult to identify due to the decaying nature of the trailing edges.

The extremely large spike occurs by virtue of the rapid rise time of the voltage pulse which causes the voltage to reach its maximum value before conduction begins. According to certain embodiments, the extreme overvoltage condition is achieved well in advance of the plasma generation tine so that a very high voltage is achieved at breakdown. This accounts for the very high current flow once conduction in the gap begins.

Figure 8:
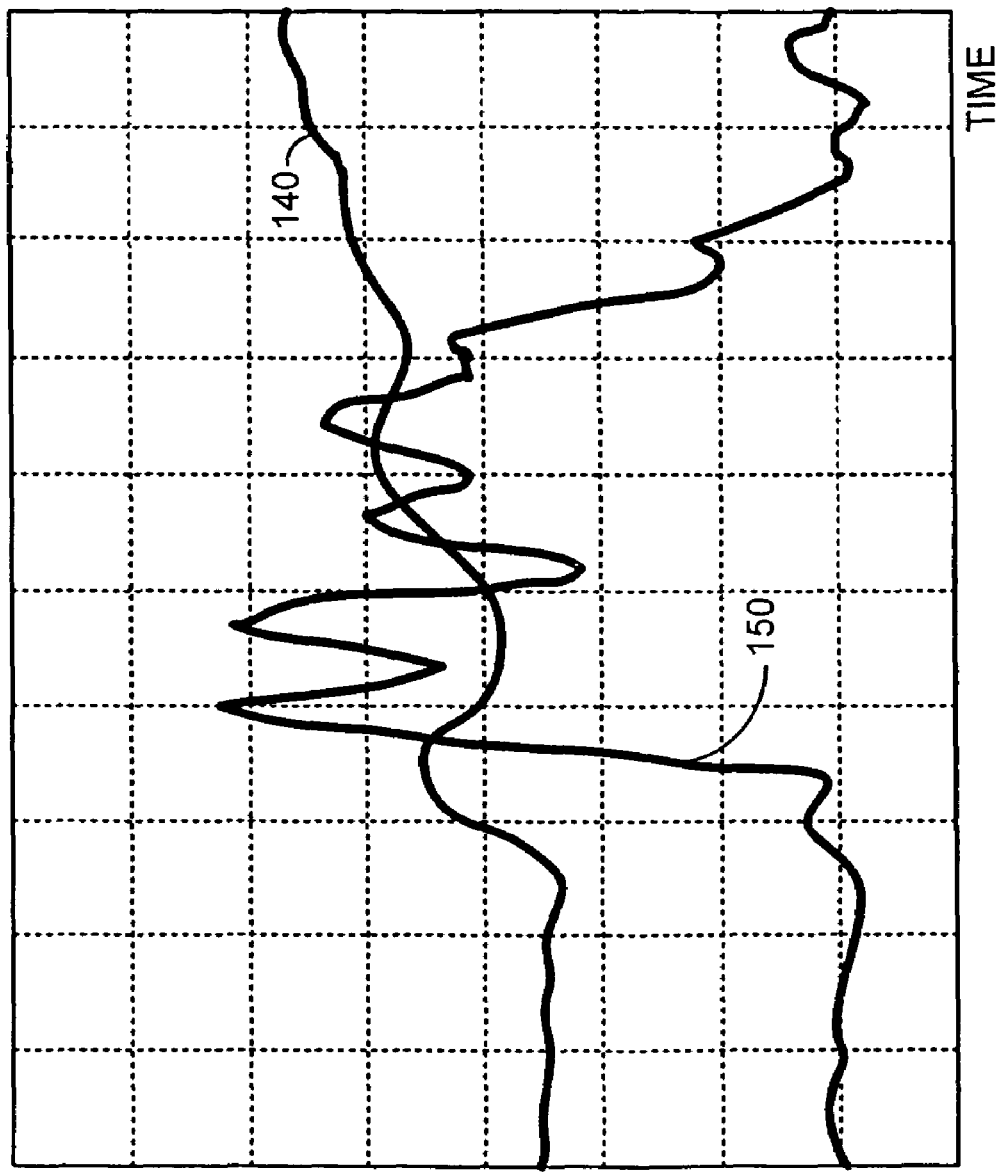
FIG. 8 is an expanded view of the waveforms illustrated in FIG. 7 using a system and methods consistent with certain embodiments of the present invention.

FIG. 8 shows an expansion of the breakdown in the spike region of the prior graph. In this graph, the voltage scale is 5 KV/division, the current scale is 10.0 Amp/division and the sweep speed is 5.0 ns/division. This illustrates that a peak current of about 40-50 A was achieved.

The traces in FIG. 7 show the high current spike at 152 followed by the pedestal current region 156. During the initial part of the current spike, as shown in FIG. 8, the current increases rapidly while the voltage begins to ramp down in accordance with the integral of the current waveform divided by the parallel capacitance. From analysis of the schematic of FIG. 6, it can be seen that the voltage drops because the stray capacitance and parallel capacitance discharges into the gap. The voltage decreases until the spike ends. The pulsed power supply then replenishes the charge on the parallel capacitor after the spike, and in the process it produces the pedestal current region. Once the dielectric capacitor is fully charged (to approximately the pulse voltage) all the currents decay to zero until the next pulse. The voltage decrease in the spike region and the voltage increase in the pedestal region are approximately linear as a function of time.

Figure 9:
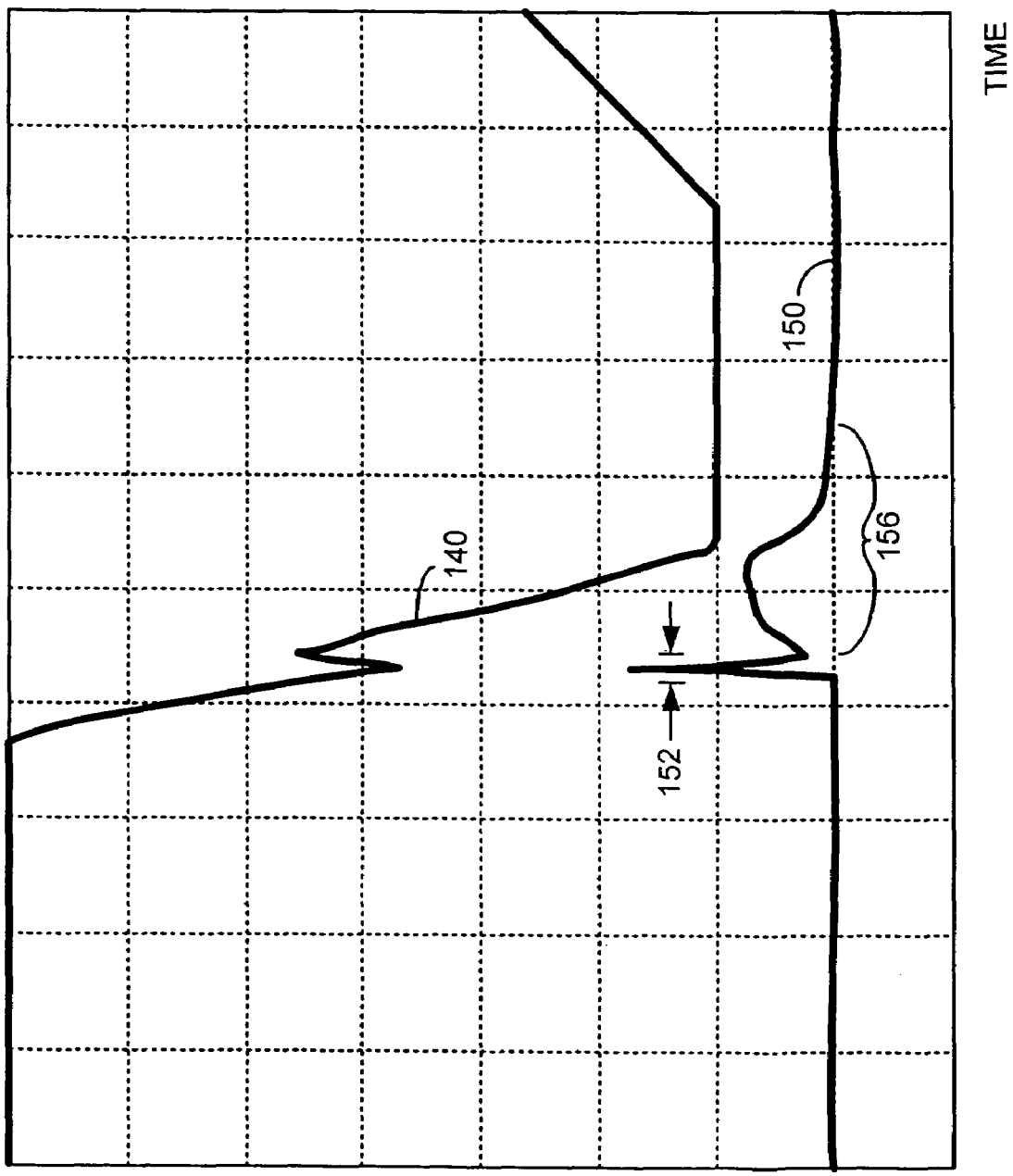
FIG. 9 is a second example of voltage and current traces using different operating conditions with the system and methods consistent with certain embodiments of the present invention.

The plasma formed by the pulse is very uniform, as observed by eye, with slight variations in current density across the surface. The variations in current density are much smaller than for filamentary discharges and any filamentary discharges that do occur do not remain in a fixed position at the electrode. The variations in the discharge will lead to many stochastically spaced spikes on the current trace. The uniformity can be seen in the current waveforms after a short conditioning period that is believed to remove impurities from the electrodes. An exemplary uniform glow waveform after conditioning is depicted in FIG. 9. The average current in the pedestal in this case is approximately 7-8 A for about 350 ns. In this trace, the current spike is relatively small because the overvoltage was small. In this case, operating parameters were adjusted to cause early breakdown on the leading edge with minimum overvoltage. However, even at the lower overvoltage condition the current waveform is very smooth, which indicates that the discharge is uniform. This set of curves was generated at a pulse repetition frequency of 300 Hz and is typical of data taken for up to 5000 Hz. In FIG. 9, the voltage scale is 5 KV/division, the current scale is 10.0 Amp/division and the sweep speed is 500 ns/division.

Figure 10:
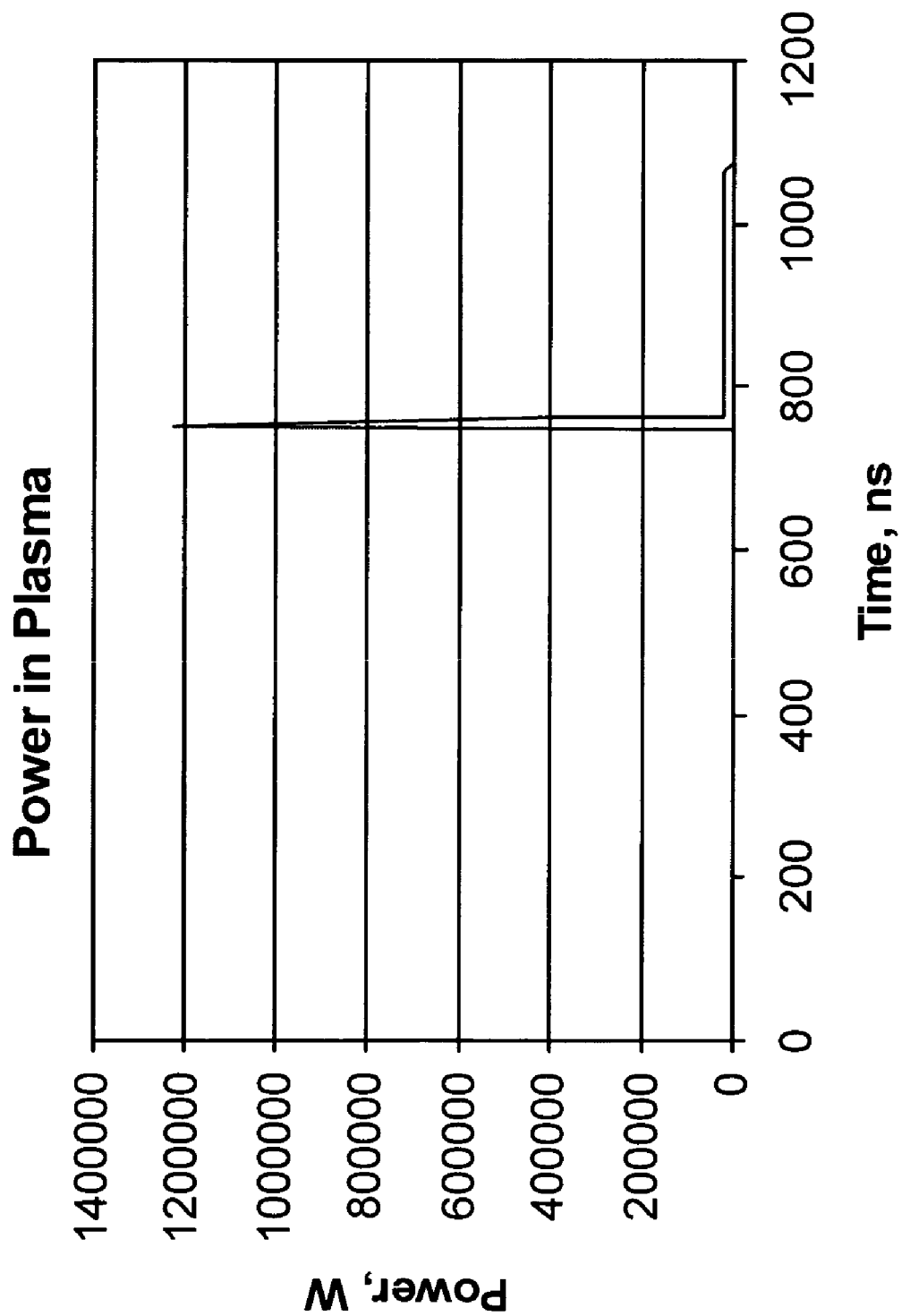
FIG. 10 is a graph of instantaneous power delivered to the discharge in an experiment carried out with a system and methods consistent with certain embodiments of the present invention.
Figure 11:
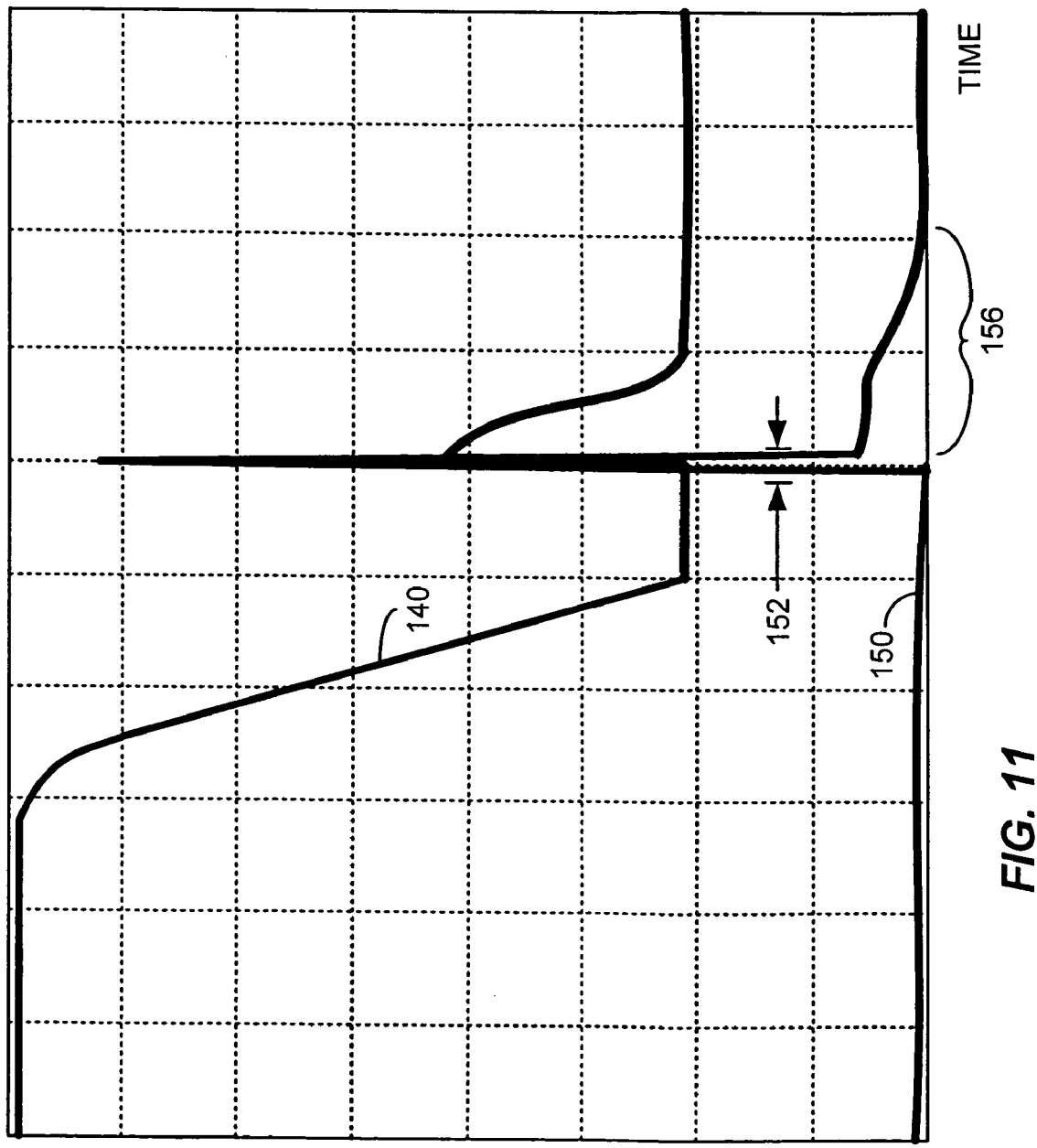
FIG. 11 is another example of the voltage and current waveforms for an experiment carried out with the system and methods consistent with certain embodiments of the present invention.

The uniformity in the current waveform is also evidence of the uniformity across the discharge area. The discharges appear to be at least as uniform as the glow-like discharges described by Golubovskii et al (Yu B. Golubovskii et al, J. Phys. D: Appl. Phys 37, 1346, 2004) who work at significantly lower voltages and power levels. The small number of filamentary discharges that are seen appear to be stochastically distributed in space and time and thereby do not remain fixed. As a result, the small number of randomly distributed filamentary discharges contribute very few (if any) localized effects on the substrate surface From an analysis of the schematic and a typical I-V curve, the power input into the discharge is approximated in the graph of FIG. 10. The instantaneous power in the plasma is based on the calculated voltage of the gap, and the I-V curves reproduced in FIG. 11. The energy deposited in the discharge by the spike and the pedestal regions are approximately equal (within a factor of 2). In FIG. 11, the voltage scale is 5 KV/division, the current scale is 10.0 Amp/division and the sweep speed is 250 ns/division.

Power such as that shown above is achieved from a system which was built to achieve fast rise time and deliver substantial current at breakdown. The fast rise time allows an extreme overvoltage condition to be developed prior to the discharge. The extreme overvoltage is responsible for the high current spike into the discharge. Increased current densities help to make the discharge more uniform. Generally speaking, the usefulness of a DBD is directly related to the dose of activated species in the plasma. The dose is the energy density or power per unit area multiplied by the time. The exceedingly large power densities in this plasma promise to make it much more effective in certain applications than most systems found in the literature.

The average energy of the electrons in the discharge is significantly higher than in other DBD systems that do not have extreme overvoltages. At sufficiently sharp rise times and overvoltages, runaway electrons are believed to be produced. (Runaway electrons are the fraction of electrons which undergoes continuous acceleration across the gap.) The threshold for runaway electrons in nitrogen, in terms of electric field/pressure, is approximately 150V/cm-Torr. The prototype used for the experiments described can operate in the 190,000V/cm regime in nitrogen, which corresponds to approximately 250V/cm-Torr. This electric field/pressure is sufficiently high to produce runaway electrons with enough potential to produce x-rays. The ions, radicals, metastables, and other excited atomic and molecular species are limited to low energies due to their larger mass and due to energy loss as a result of collisions with neutral gas particles.

Without a fast rise time (i.e., fast enough to produce extreme overvoltage prior to the discharge), no extreme overvoltage can occur and the discharge is limited to DC breakdown voltages. The most efficient discharge in terms of overall current, excited species, high dose etc. is expected to be a pulsed system with a fast rise time. The plasma system described can be operated at atmospheric pressure (as well as other pressures) using $N_2$, air, $O_2$, Ar, Kr, Ne, He, $SF_6$, $CF_4$, $CO_2$, CO, acetylene, or any mixture of these or many other gases.

The use of $SF_6$ highlights the benefit of using the fast rise time pulsed system. $SF_6$ is a high dielectric constant gas with a high breakdown voltage and is frequently used to stop discharge formation. Its breakdown voltage is higher than the breakdown voltage of the other gases mentioned. It is thus a very difficult gas in which to produce a glow discharge. However, as with all gases tested, a high current discharge in $SF_6$ was easily obtained using the present prototype system. All gases examined have produced acceptable results as a discharge gas. The discharge can also be operated under vacuum or even higher than atmospheric pressures. Certain benefits of systems such as the prototype system described are best seen at higher pressures, but embodiments consistent with the present invention are in no way limited to any pressure range.

A range of possible applications for this plasma technology is listed below. Plasma systems have been used in many of these instances, while others of the applications are merely theorized at present, and it is anticipated that the present plasma system can similarly be used. Such applications include, but are not limited to, plasma sterilization, blood plasma sterilization, ozone generation, Excimer lamps and lasers, surface modification and functionalization, surface cleaning of organic residues, reactive ion etching of materials, plasma enhanced chemical vapor deposition of materials, enhanced atomic layer deposition, enhanced catalysis, plasma polymerization, hydrogen production by stripping hydrogen from larger molecules, plasma displays, air pollution abatement and remediation, to mention a few. Systems consistent with the present invention can be used in combination with other apparatus such as a substrate heater, a sample loading system, or a continuous feed system for processing rolls of material. One example would include sterilization of coated paper product surfaces (e.g., milk carton material).

In accordance with certain embodiments consistent with the present invention, the plasma voltage and current traces show a spike formed at the start of the discharge, followed by a pedestal current region that continues until the dielectric is fully charged. The discharge then shuts off. This is in contrast to other systems in which the current shuts off immediately after the original spike. The extreme overvoltage undergoes a voltage decrease during the initial spike. The power supply then replenishes the voltage and thereby produces the pedestal current region in the gap. The pedestal region appears to be unique to systems with such an extreme overvoltage condition and robust power supply.

The extreme overvoltage occurs because the voltage rise time is fast enough for the voltage to reach extreme overvoltage during the lag time preceding the formation of the discharge. Thus the voltage applied across the electrode gap is substantially greater than the normal DC breakdown voltage at any electrode spacing. This helps produce a normal, glow-like plasma and avoids the generation of high current filaments. Filaments are easily formed in low current discharges because, small areas of the dielectric may be charged independently. At very high current densities, there is no chance for widely separated charges to funnel into a single point. Dumping the total charge on the dielectric, in effect, forces the spreading of charge in a uniform manner across the surface.

In accordance with certain embodiments, various attributes of the discharge have been observed and these can be enhanced to suit the requirements for particular applications. Many of these attributes may be advantageous for various applications. By way of example, and without any suggestion that any or all of the present attributes are necessary conditions which are present in any given embodiment, the following observations (and associated theories) are presented:

1. The DBD discharge created by the pulsed system forms two distinct plasma regions which are a.) an initial high current spike, followed by b.) a longer duration lower current pedestal region.
2. The present prototype has demonstrated the highest known instantaneous power in the spike region. Instantaneous discharge power of $\geq 1$ MW in the spike region and instantaneous discharge power of $\geq 23$ kW in the pedestal region have been achieved.
3. The large spike power appears to be due to the overvoltage created by the fast rise time of the pulsed power supply and the parallel capacitance in the system which discharges rapidly into the gap. Tuning the parallel capacitance should permit variation in the size and shape of the initial spike. This allows tuning of the spike for various applications.
4. A pulse sharpener can be used to decrease the rise time, thereby increasing the overvoltage, and thereby increasing the spike and pedestal power.
5. The noted pedestal region's instantaneous and total power is unprecedented. The pedestal region is created because the power supply must replenish the voltage that is initially discharged in the spike region. The prototype power supply design is believed to provide the rapid voltage replenishment which gives rise to a pedestal current.
6. To date, the highest DBD current density achieved has been approximately 10 A/cm$^2$. This is dramatically higher than known systems are able to produce. More power means higher dose and faster operation for most applications.
7. The high peak power and low average power in the system provides substantial instantaneous gas heating, while the average gas temperature and work-piece can be kept cool.
8. The system can be scaled almost linearly with electrode size, i.e., the characteristics of the plasma will be nearly identical if the available power is scaled with the electrode area.
9. The sharp rise time which produces the extreme overvoltage is also believed to increase the average electron energy some of which attain high electron energies which are believed to be runaway electrons. This system is believed to produce runaway electrons which may provide beneficial aspects in certain applications such as plasma sterilization.
10. The runaway electrons produced when an extreme overvoltage condition is used to produce the plasma are believed to have the necessary energy to produce x-rays.
11. A combined RF and pulsed power supply can potentially be used to achieve higher overvoltages without altering the pulse generator. This increases the power to the pulses and increases the energy of the electrons. A synchronizer can be used for timing the generation of pulsed voltage so that pulses are applied at the most beneficial part of the RF voltage waveform.
12. The high voltage attainable with this system provides a larger working distance (gap) than with known conventional RF DBD systems. A working gap of 7-8 mm has been used successfully during nitrogen plasma generation using the present pulsed mode power supply.
13. The prototype DBD system appears to be capable of using virtually any gas and has been used with the following gases and mixtures of gases: $N_2$, air, $O_2$, Ar, Kr, Ne, He, $SF_6$, $CF_4$, $CO_2$, CO, and acetylene.
14. A shock wave is believed to be created in the plasma due to the deposition of power in the working gas over a shorter time than the acoustic transit time in the gas. Therefore, in some instances, a container is required to contain small particles being treated so that the shock wave does not move them from the working area. As noted, this shock may be useful for agitation or other purposes.

Figure 12:
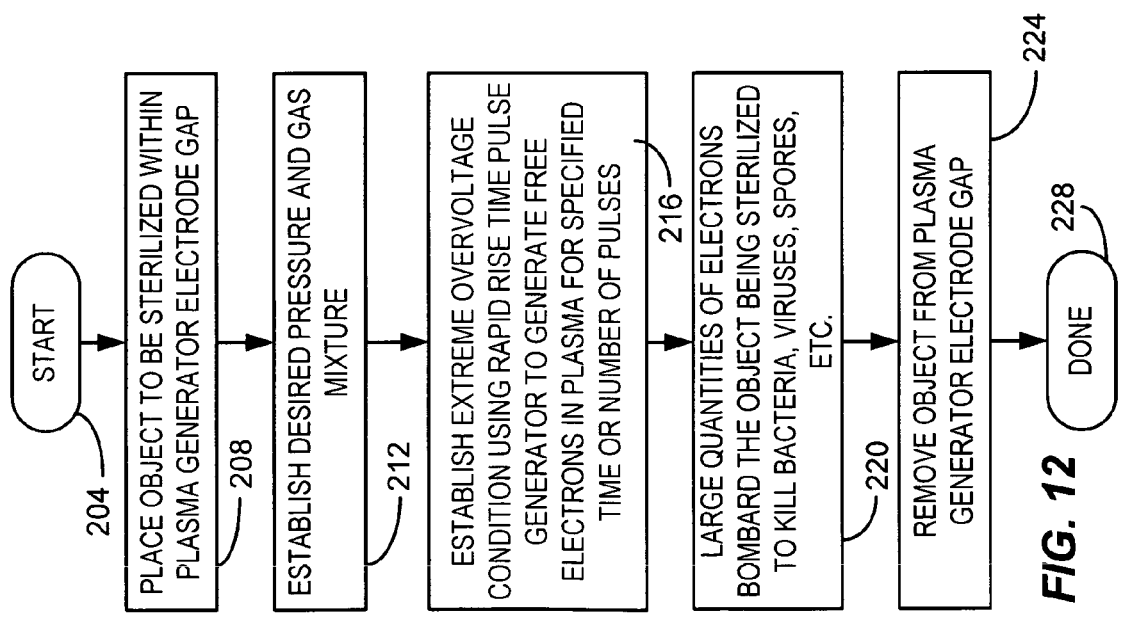
FIG. 12 is a flow chart of a sterilization process consistent with certain embodiments of the present invention.

Embodiments consistent with the present invention may be well suited for sterilization applications. In order to achieve sterilization, a process such as that depicted in FIG. 12 can be used, starting at 204. An object of matter (whether solid, liquid, gas, etc.) to be sterilized is placed within the gap of the plasma generator. A desired mixture of gasses is provided at 212 as an environment for the discharge. In experiments to date, the gas environment does not seem to be critical. An extreme overvoltage condition is then created across the gap by using a rapid rise time pulse generator at 216. This process has been used to treat the object at 220 and to kill bacteria and possibly other virulent biological materials. After a prescribed time, which can be determined experimentally, the sterilized object can be removed from the electrode gap at 224. The process ends at 228. It is believed that the electrons produced in the system are responsible for the very rapid sterilization. This is the first known use of electrons extracted from a plasma to achieve sterilization.

Sterilization has been successfully carried out using the prototype device described above. Consider, for example, the following experiments:

EXAMPLE

Figure 13:
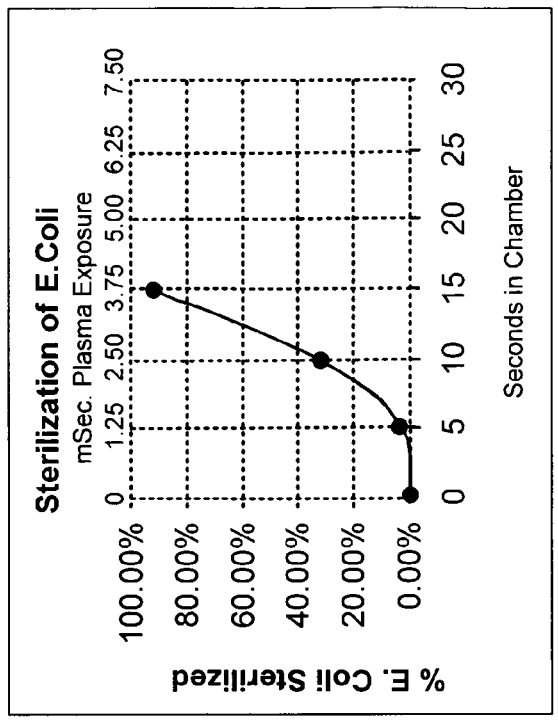
FIG. 13 is a graph illustrating the sterilization of *E. coli* that occurred in a sterilization experiment carried out with the system and methods consistent with certain embodiments of the present invention.

An example of the effects of sterilization is given below. An experiment on E. Coli bacteria was performed using a nitrogen plasma operated at 22 kV, a 3-4 mm electrode gap spacing, approximately 10 A spike current and approximately 2 A peak pedestal current. The pulse repetition rate was approximately 300 pulses per second, thus the overall exposure to the plasma represents a relatively small percentage of the time. E. Coli was deposited on polystyrene substrates and exposed to the plasma for 5, 10, and 15 seconds total time. Other samples were exposed for minutes rather than seconds. When cultured using an agar solution for 3 days at room temperature, the control samples showed on average 500 colonies of bacteria on the surface. When the exposed samples were cultured using the same conditions, the results are shown in FIG. 13. All exposures greater than approximately 30 seconds resulted in no detectable colonies. As can be seen from the graph of FIG. 13, the actual time of exposure to the plasma for each test sample was approximately 1.25 mS, 2.5 mS and 3.75 mS respectively for 5, 10 and 15 seconds of total time in the chamber. Thus, in a more optimized system, actual time of exposure could be dramatically shortened by increases in the pulse repetition rate.

Sterilization using plasma discharges based on the generation and utilization of ions, ozone, and ultraviolet (UV) radiation is known. In a nitrogen plasma 316 nm is the lowest energy UV wavelength observed. Based upon the literature UV exposure at this energy does not account for this dramatic reduction of the bacteria population in this short exposure time. Ozone exposure, and thermal exposure, both well known methods of sterilization, do not appear to account for the dramatic reduction of the bacteria population in this short period of exposure since only trace amounts of oxygen containing gases are present and the average gas temperature remains low. It is believed that the average ion energies in the plasma are very low and not sufficient to completely penetrate the cell walls. Ions could erode the cell wall through ion sputtering given enough time at low energies. There are accounts of the use of reactive gases in the plasma to generate ions and free radicals that are chemically very reactive and which quickly react with and erode the cell wall. However, nitrogen has not been described for this purpose because it is well known that nitrogen is not as corrosive to organic materials as oxygen, hydroxide, or other oxygen bearing species. It is therefore believed that the cause of the sterilization is bombardment of the cells by electrons that penetrate and destroy the cells.

Two anecdotal experiments appear to further confirm this hypothesis. In these experiments, sterilization of E. Coli was carried out in an inoculated culturing media manufactured by 3M corporation in one experiment. In another experiment, samples of 3 ml of water were sterilized using the plasma. In the water experiment, it was observed that the water moved and flattened out into a film during exposure to the plasma. In both cases, sterilization was achieved. It is believed that the electrons have the requisite energy and are responsible for the observed sterilization.

Thus, a dielectric barrier plasma discharge device consistent with certain embodiments of the present invention has a pair of electrodes spaced apart by an electrode gap. A dielectric is disposed between the electrodes. The electrode gap is provided with a gas at a specified pressure. A rapid rise time voltage pulse generator produces a voltage pulse across the electrodes to cause an extreme overvoltage condition, wherein the rapid rise time is less than the plasma generation time so that the extreme overvoltage condition occurs prior to current flow across the electrode gap. The resulting plasma can be utilized to carry out many potential tasks including, but not limited to sterilization.

A method of generating a glow discharge plasma, consistent with certain embodiments hereof involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage condition, wherein the rapid rise time is less than a plasma generation time so that the extreme overvoltage condition occurs prior to current flow across the electrode gap.

A method of generating a glow discharge plasma for sterilization consistent with certain embodiments involves providing a pair of electrodes spaced apart by an electrode gap, and having a dielectric disposed in the electrode gap between the electrodes; placing the electrodes within an environment wherein the electrode gap can be provided with a gas at a specified pressure; applying a rapid rise time voltage pulse across the electrodes to cause an extreme overvoltage condition, wherein the rapid rise time is less than a plasma generation time so that the extreme overvoltage condition occurs prior to current flow across the electrode gap; and exposing an object of matter to the plasma for a specified time, thereby sterilizing the object.

A dielectric barrier plasma discharge device consistent with certain embodiments has a pair of electrodes spaced apart by an electrode gap. A dielectric is disposed between the electrodes. The electrode gap is provided with a gas at a specified pressure. A rapid rise time voltage pulse generator produces a voltage pulse across the electrodes to cause an extreme overvoltage condition, wherein runaway electrons are generated in the plasma.

A method of generating a glow discharge plasma consistent with certain embodiments involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage condition wherein a runaway electron condition is generated in the electrode gap.

A dielectric barrier plasma discharge device consistent with certain embodiments has a pair of electrodes spaced apart by an electrode gap. A dielectric disposed between the electrodes. The electrode gap is provided with a gas at a specified pressure. A rapid rise time voltage pulse generator produces a voltage pulse across the electrodes to cause an extreme overvoltage condition, wherein a shock wave is produced in the plasma.

A method of generating a glow discharge plasma involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage condition wherein a shock wave is generated in a plasma generated in the electrode gap.

A dielectric barrier plasma discharge device consistent with certain embodiments has a pair of electrodes spaced apart by an electrode gap. A dielectric disposed between the electrodes. The electrode gap is provided with a gas at a specified pressure. A rapid rise time voltage pulse generator produces a voltage pulse across the electrodes to cause an extreme overvoltage condition, whereby, current flowing between the electrodes can be characterized by an initial spike in current followed by a pedestal region wherein current continues to flow after the initial spike in current.

A method of generating a glow discharge plasma involves providing a pair of electrodes spaced apart by an electrode gap, and having a dielectric disposed in the electrode gap between the electrodes; placing the electrodes within an environment wherein the electrode gap can be provided with a gas at a specified pressure; and applying a rapid rise time voltage pulse across the electrodes to cause an extreme overvoltage, whereby, current flowing between the electrodes can be characterized by an initial spike in current followed by a pedestal region wherein current continues to flow after the initial spike in current.

A method of sterilizing an object of matter in a manner consistent with certain embodiments involves generating a plasma exhibiting a runaway electron condition; and exposing the object of matter to the plasma for a specified time, whereby the object is bombarded with high energy electrons to sterilize the object.

In the above methods and apparatus, it is thus believed that an object can be exposed to the plasma for a specified time, in order to effect at least one of the following: plasma sterilization, blood plasma sterilization, Ozone generation, surface modification and functionalization, surface cleaning of organic residues, reactive ion etching of materials, plasma enhanced chemical vapor deposition materials, enhanced atomic layer deposition, enhanced catalysis, plasma polymerization, hydrogen production from stripping of hydrogen from larger molecules, plasma displays, air pollution abatement and air pollution remediation. It is further believed that generating excited species in the plasma can be used to produce one of the following: an Excimer lamp, lasers, and a CO2 lasers.

In actual experiments conducted, helium, nitrogen, argon, crypton CF4, SF6, acetylene, TiCL4, and air were all easily discharged at atmospheric pressures. It is thus believed that any number of gasses can be utilized, including but not limited to: air, Sulfur Hexafluoride ($SF_6$), Nitrogen, Oxygen, Carbon tetrafluoride ($CF_4$), acetylene, Helium, Neon, Argon, Krypton, Xenon, or mixtures of any of these gases.

Etching gases that can potentially be used include Fluorinated gases for semiconductor etching applications may be used such as $CF_4$, $SF_6$, $CHF_3$, nitrogen trifluoride ($NF_3$), and hydrofluoric acid (HF). Also chlorinated gases used for etching applications such as boron trichloride ($BCl_3$), Chlorine ($Cl_2$), and hydrochloric acid (HCl). Also hydrogen containing gases used in etching such as ammonia ($NH_3$), methane ($CH_4$), and alcohols such as methanol ($CH_3OH$) can potentially be used. PECVD gases such as Si containing gases may potentially be used such as silane ($SiH_4$), disilane ($Si_2H_6$), and dichlorosilane ($SiH_2Cl_2$), tetraethylorthosilicate (TEOS) and other ortho silicate gases.

Other semiconductor gases (the gas is not a semiconductor but is used in the deposition of semiconductor materials) such as Germane ($GeH_4$), zinc chloride ($ZnCl_2$), dimethylzinc (DMZn), trimethylgallium (TMGa), gallium trichloride ($GaCl_3$), hydrogen sulfide ($H_2S$), and arsine ($AsH_3$) can also potentially be used.

Metal containing gases such as tantalum pentafluoride ($TaF_5$), tungsten hexafluoride ($WF_6$), titanium tetreachloride ($TiCL_4$), molybdenum hexafluoride ($MoF_6$), aluminum chloride ($AlCl_3$), aluminum acetylacetate, copper acetonylacetonate, nickel acetate, nickel carbonyl, hafnium chloride ($HfCl_4$), and other metal containing gases can potentially be used. Carbon containing gases such as methane, ethane, propane, etc. can potentially be used.

Sterilization gases such as oxygen, nitrogen, air, ozone, HCl, KOH, He, Ne, Ar, or mixtures of these gases can potentially be used.

Functionalization can potentially be carried out using the fluorinated gases such as CHF3, CF4, to add F to surfaces or gases containing hydroxyl groups such as acetic acid, water, alcohols, or other larger molecular groups to add hydroxyl groups to surfaces.

Other gases that are not readily available in the gas phase may be boiled from the liquid phase an introduced into the plasma system. For example water may be boiled to produce steam which can be introduced to the chamber with or without a dry carrier gas.

To summarize, the gas used is dependent upon the work that is desired to be carried out by or in the plasma. Many other gasses may be used without limitation.

Many variations will occur to those skilled in the art upon consideration of the present teachings. While certain embodiments herein were described in conjunction with specific circuitry that carries out the functions described, other embodiments are contemplated in which other circuitry can be used to carry out the functions described. As noted above, much of this discussion has involved theory of operation that has not yet been fully explored and proven, thus, the claims should not be restricted on the basis of the disclosed theory.

While certain illustrative embodiments have been described, it is evident that many alternatives, modifications, permutations and variations will become apparent to those skilled in the art in light of the foregoing description.

What is claimed is:

1. A method of generating a glow discharge plasma, comprising:

providing a pair of electrodes spaced apart by an electrode gap, and having a dielectric disposed in the electrode gap between the electrodes;

placing the electrodes within an environment wherein the electrode gap is provided with a gas at a specified pressure; and applying a rapid rise time voltage pulse across the electrodes to cause an extreme overvoltage condition, wherein the rapid rise time is less than a plasma generation time so that the extreme overvoltage condition occurs prior to current flow across the electrode gap, and wherein current flowing between the electrodes is characterized by an initial spike in current followed by a pedestal region wherein current continues to flow after the initial spike in current.

2. The method according to claim 1, wherein the overvoltage condition is caused by a peak value of the voltage pulse that exceeds a threshold voltage needed to generate plasma in the electrode gap by a factor of at least 1.5 times the threshold voltage.

3. The method according to claim 1, wherein the overvoltage condition is caused by a peak value of the voltage pulse that exceeds two times a threshold voltage needed to generate plasma in the electrode gap.

4. The method according to claim 1, wherein the overvoltage condition is caused by a peak value of the voltage pulse that exceeds three times a threshold voltage needed to generate plasma in the electrode gap.

5. The method according to claim 1, wherein the gas comprises a gas selected from the group consisting of: air, Sulfur Hexafluoride (SF6), Nitrogen, Oxygen, Carbon tetrafluoride ($CF_4$), acetylene, Helium, Neon, Argon, Krypton, Xenon, $CF_4$, $SF_6$, $CHF_3$, nitrogen trifluoride ($NF_3$), and hydrofluoric acid (HF), boron trichioride ($BCl_3$), Chlorine ($Cl_2$), and hydrochloric acid (HCl), ammonia ($NH_3$), methane ($CH_4$), and alcohols such as methanol ($CH_3OH$), silane ($SiH_4$), disilane ($Si_2H_6$), and dichiorosilane ($SiH_2Cl_2$), tetraethylorthosilicate (TEOS), ortho silicate gases, Germane ($GeH_4$), zinc chloride ($ZnCl_2$), dimethylzinc (DMZn), trimethylgallium (TMGa), gallium trichloride ($GaCl_3$), hydrogen sulfide ($H_2S$), and arsine ($AsH_3$), tantalum pentafluoride ($TaF_5$), tungsten hexafluoride ($WF_6$), titanium tetreachioride ($TiCl_4$), molybdenum hexafluoride ($MoF_6$), aluminum chloride ($AlCl_3$), aluminum acetylacetate, copper acetonylacetonate, nickel acetate, nickel carbonyl, hafnium chloride ($HfCl_4$), methane, ethane, propane, ozone, HCl, KOH, He, Ne, Ar, CHF3, CF4, gases containing hydroxyl groups, hydrogen containing gases, PECVD gases, semiconductor gases, Metal containing gases, fluorinated gases, gasses that are boiled from the liquid phase, and mixtures of the above gasses.

6. The method according to claim 1, wherein the specified pressure is in the range of approximately one atmosphere to less than 0.1 atmosphere.

7. The method according to claim 1, further comprising exposing an object of matter to the plasma for a specified time, in order to effect at least one of the following: plasma sterilization, blood plasma sterilization, Ozone generation, surface modification and functionalization, surface cleaning of organic residues, reactive ion etching of materials, plasma enhanced chemical vapor deposition materials, enhanced atomic layer deposition, enhanced catalysis, plasma polymerization, hydrogen production from stripping of hydrogen from larger molecules, plasma displays, air pollution abatement and air pollution remediation.

8. An object processed by exposure to a plasma generated by the method according to claim 7.

9. The method according to claim 1, further comprising generating excited species in the plasma to produce one of the following: an Eximer lamp, a lasers, and a CO2 lasers.

10. A plasma generated using a method comprising:
providing a pair of electrodes spaced apart by an electrode gap, and having a dielectric disposed in the electrode gap between the electrodes;
placing the electrodes within an environment wherein the electrode gap is provided with a gas at a specified pressure; and
applying a rapid rise time voltage pulse across the electrodes to cause an extreme overvoltage condition, wherein the rapid rise time is less than a plasma generation time so that the extreme overvoltage condition occurs prior to current flow across the electrode gap, and wherein current flowing between the electrodes is characterized by an initial spike in current followed by a pedestal region wherein current continues to flow after the initial spike in current to produce the plasma.

11. The method according to claim 1, wherein the plasma induces a reaction in an object of matter exposed to the plasma, and wherein the reaction includes one of chemical vapor deposition, polymerization, atomic layer deposition, and electron induced decomposition.

12. A method of generating a glow discharge plasma, comprising:
providing a pair of electrodes spaced apart by an electrode gap, and having a dielectric disposed in the electrode gap between the electrodes;
placing the electrodes within an environment wherein the electrode gap is provided with a gas at a specified pressure;
applying a rapid rise time voltage pulse across the electrodes to cause an extreme overvoltage condition, wherein the rapid rise time is less than a plasma generation time so that the extreme overvoltage condition occurs prior to current flow across the electrode gap, and wherein current flowing between the electrodes is characterized by an initial spike in current followed by a pedestal region wherein current continues to flow after the initial spike in current; and
exposing an object of matter to the plasma for a specified time, thereby sterilizing the object.

13. The method according to claim 12, further comprising disposing a capacitor substantially in parallel with the pair of electrodes.

14. The method according to claim 12, wherein the overvoltage condition leads to a runaway electron condition, and wherein the sterilizing is a result of the object of matter being bombarded by high energy electrons.

15. The method according to claim 12, wherein the overvoltage condition is caused by a peak value of the voltage pulse that exceeds approximately 1.5 times a threshold voltage needed to generate plasma in the electrode gap.

16. The method according to claim 12, wherein the specified pressure is in the range from approximately 1 atmosphere to less than 0.1 atmospheres.

17. An object of matter sterilized by a method comprising:
providing a pair of electrodes spaced apart by an electrode gap, and having a dielectric disposed in the electrode gap between the electrodes;
placing the electrodes within an environment wherein the electrode gap is provided with a gas at a specified pressure;
applying a rapid rise time voltage pulse across the electrodes to cause an extreme overvoltage condition, wherein the rapid rise time is less than a plasma generation time so that the extreme overvoltage condition occurs prior to current flow across the electrode gap, and wherein current flowing between the electrodes is characterized by an initial spike in current followed by a pedestal region wherein current continues to flow after the initial spike in current; and
exposing the object of matter to the plasma for a specified time, thereby sterilizing the object of matter.

18. A dielectric barrier plasma discharge device, comprising:
a pair of electrodes spaced apart by an electrode gap;
a dielectric disposed between the electrodes;
wherein the electrode gap is provided with a gas at a specified pressure; and
a rapid rise time voltage pulse generator that produces a voltage pulse across the electrodes to cause an extreme overvoltage condition, wherein the rapid rise time is less than a plasma generation time so that the extreme overvoltage condition occurs prior to current flow across the electrode gap, and wherein current flowing between the electrodes is characterized by an initial spike in current followed by a pedestal region wherein current continues to flow after the initial spike in current.

19. The dielectric barrier plasma discharge device according to claim 18, further comprising a capacitor disposed substantially in parallel with the pair of electrodes.

20. The dielectric barrier plasma discharge device according to claim 18, wherein the pulse generator further comprises a pulse shaping circuit that enhances the rise time of the voltage pulse across the electrodes.

21. The dielectric barrier plasma discharge device according to claim 18, wherein the overvoltage condition is caused by a peak value of the voltage pulse that exceeds 1.5 times a threshold voltage needed to generate plasma in the electrode gap.

22. The dielectric barrier plasma discharge device according to claim 18, wherein the overvoltage condition is caused by a peak value of the voltage pulse that exceeds two times a threshold voltage needed to generate plasma in the electrode gap.

23. The dielectric barrier plasma discharge device according to claim 18, wherein the overvoltage condition is caused by a peak value of the voltage pulse that exceeds three times a threshold voltage needed to generate plasma in the electrode gap.

24. The dielectric barrier plasma discharge device according to claim 18, wherein the specified pressure is in the range from approximately 1 atmosphere to less than 0.1 atmospheres.

25. A plasma generated using the dielectric barrier plasma discharge device according to claim 18.

26. The dielectric barrier plasma discharge device according to claim 18, wherein the plasma induces a reaction in an object of matter exposed to the plasma, and wherein the reaction includes one of chemical vapor deposition, polymerization, atomic layer deposition, and electron induced decomposition.

27. A dielectric barrier plasma discharge device, comprising:
   a pair of electrodes spaced apart by an electrode gap;
   a dielectric disposed between the electrodes;
   wherein the electrode gap is provided with a gas at a specified pressure; and
   a rapid rise time voltage pulse generator that produces a voltage pulse across the electrodes to cause an extreme overvoltage condition, wherein runaway electrons are generated in a plasma, and wherein current flowing between the electrodes is characterized by an initial spike in current followed by a pedestal region wherein current continues to flow after the initial spike in current.

28. The dielectric barrier plasma discharge device according to claim 27, further comprising a capacitor disposed substantially in parallel with the pair of electrodes for tuning electron energy in the runaway electrons.

29. The dielectric barrier plasma discharge device according to claim 27, wherein the pulse generator further comprises a pulse shaping circuit that enhances the rise time of the voltage pulse across the electrodes.

30. The dielectric barrier plasma discharge device according to claim 27, wherein the overvoltage condition is caused by a peak value of the voltage pulse that exceeds at least 1.5 times a threshold voltage needed to generate plasma in the electrode gap.

31. The dielectric barrier plasma discharge device according to claim 27, wherein the specified pressure is in the range from approximately 1 atmosphere to less than 0.1 atmospheres.

32. An object of matter processed by exposure to a plasma generated using a device according to claim 27.

33. The dielectric barrier plasma discharge device according to claim 27, wherein the runaway electrons have sufficient energy to produce x-rays.

34. The dielectric barrier plasma discharge device according to claim 27, wherein the plasma induces a reaction in an object of matter exposed to the plasma, and wherein the reaction includes one of chemical vapor deposition, polymerization, atomic layer deposition, and electron induced decomposition.

35. A plasma generated by a dielectric barrier plasma discharge device, wherein the dielectric barrier plasma discharge device comprises:
   a pair of electrodes spaced apart by an electrode gap;
   a dielectric disposed between the electrodes;
   wherein the electrode gap is provided with a gas at a specified pressure; and
   a rapid rise time voltage pulse generator that produces a voltage pulse across the electrodes to cause an extreme overvoltage condition, wherein runaway electrons are generated in the plasma, and wherein current flowing between the electrodes is characterized by an initial spike in current followed by a pedestal region wherein current continues to flow after the initial spike in current to produce the plasma.

36. A method of generating a glow discharge plasma, comprising:
   providing a pair of electrodes spaced apart by an electrode gap, and having a dielectric disposed in the electrode gap between the electrodes;
   placing the electrodes within an environment wherein the electrode gap is provided with a gas at a specified pressure; and
   applying a rapid rise time voltage pulse across the electrodes to cause an extreme overvoltage condition leading to a runaway electron condition in the electrode gap, wherein current flowing between the electrodes is characterized by an initial spike in current followed by a pedestal region wherein current continues to flow after the initial spike in current.

37. The method according to claim 36, wherein the overvoltage condition is caused by a peak value of the voltage pulse that exceeds at least 1.5 times a threshold voltage needed to generate plasma in the electrode gap.

38. The method according to claim 36, wherein the specified pressure is less than or equal to approximately one atmosphere.

39. The method according to claim 36, wherein a capacitor is disposed substantially in parallel with the pair of electrodes, and further comprising tuning electron energy in runaway electrons by selection of a value of said capacitor.

40. The method according to claim 36, wherein runaway electrons have sufficient energy to produce x-rays.

41. The method according to claim 36, wherein the plasma induces a reaction in an object of matter exposed to the plasma, and wherein the reaction includes one of polymerization, atomic layer deposition, electron induced desorption, and surface heating.

42. An object processed by exposure to a plasma generated by the method according to claim 36.

43. A dielectric barrier plasma discharge device, comprising:
   a pair of electrodes spaced apart by an electrode gap;
   a dielectric disposed between the electrodes;
   wherein the electrode gap is provided with a gas at a specified pressure; and
   a rapid rise time voltage pulse generator that produces a voltage pulse across the electrodes to cause an extreme overvoltage condition, wherein a shock wave is generated in a plasma generated in the electrode gap, and wherein current flowing between the electrodes are characterized by an initial spike in current followed by a pedestal region wherein current continues to flow after the initial spike in current.

44. The dielectric barrier plasma discharge device according to claim 43, wherein the overvoltage condition is caused by a peak value of the voltage pulse that exceeds at least 1.5 times a threshold voltage needed to generate plasma in the electrode gap.

45. The dielectric barrier plasma discharge device according to claim 43, wherein the specified pressure is less than or equal to approximately one atmosphere.

46. The dielectric barrier plasma discharge device according to claim 43, further comprising a capacitor disposed substantially in parallel with the pair of electrodes for tuning electron energy in runaway electrons.

47. The dielectric barrier plasma discharge device according to claim 43, wherein the pulse generator further comprises a pulse shaping circuit that enhances the rise time of the voltage pulse across the electrodes.

48. An object of matter sterilized by exposure to a plasma generated using the device according to claim 43.

49. The dielectric barrier plasma discharge device according to claim 43, wherein the plasma induces a reaction in an object of matter exposed to the plasma, and wherein the reaction includes one of chemical vapor deposition, polymerization, atomic layer deposition, and electron induced decomposition.

50. A method of generating a glow discharge plasma, comprising:
  providing a pair of electrodes spaced apart by an electrode gap, and having a dielectric disposed in the electrode gap between the electrodes;
  placing the electrodes within an environment wherein the electrode gap is provided with a gas at a specified pressure; and
  applying a rapid rise time voltage pulse across the electrodes to cause an extreme overvoltage condition wherein a shock wave is produced in a plasma generated in the electrode gap, and wherein current flowing between the electrodes is characterized by an initial spike in current followed by a pedestal region wherein current continues to flow after the initial spike in current.

51. The method according to claim 50, wherein the overvoltage condition is caused by a peak value of the voltage pulse that exceeds at least 1.5 times a threshold voltage needed to generate plasma in the electrode gap.

52. The method according to claim 50, wherein a capacitor is disposed substantially in parallel with the pair of electrodes, and further comprising tuning electron energy in runaway electrons by selection of a value of said capacitor.

53. An object of matter processed, by exposure to a plasma generated by the method according to claim 50.

54. The method according to claim 50, wherein the plasma induces a reaction in an object of matter exposed to the plasma, and wherein the reaction includes one of chemical vapor deposition, polymerization, atomic layer deposition, and electron induced decomposition.

55. A dielectric barrier plasma discharge device, comprising:
  a pair of electrodes spaced apart by an electrode gap;
  a dielectric disposed between the electrodes;
  wherein the electrode gap is provided with a gas at a specified pressure; and
  a rapid rise time voltage pulse generator that produces a voltage pulse across the electrodes to cause an extreme overvoltage condition, whereby, current flowing between the electrodes is characterized by an initial spike in current followed by a pedestal region wherein current continues to flow after the initial spike in current.

56. The dielectric barrier plasma discharge device according to claim 55, wherein the overvoltage condition is caused by a peak value of the voltage pulse that exceeds at least 1.5 times a threshold voltage needed to generate plasma in the electrode gap.

57. The dielectric barrier plasma discharge device according to claim 55, wherein the specified pressure is less than or equal to approximately one atmosphere.

58. The dielectric barrier plasma discharge device according to claim 55, further comprising a capacitor disposed substantially in parallel with the pair of electrodes for tuning electron energy in runaway electrons.

59. The dielectric barrier plasma discharge device according to claim 55, wherein the pulse generator further comprises a pulse shaping circuit that enhances the rise time of the voltage pulse across the electrodes.

60. An object of matter processed by exposure to a plasma generated using a device according to claim 55.

61. The dielectric barrier plasma discharge device according to claim 55, wherein the plasma induces a reaction in an object of matter exposed to the plasma, and wherein the reaction includes one of chemical vapor deposition, polymerization, atomic layer deposition, and electron induced decomposition.

62. A method of generating a glow discharge plasma, comprising:
  providing a pair of electrodes spaced apart by an electrode gap, and having a dielectric disposed in the electrode gap between the electrodes;
  placing the electrodes within an environment wherein the electrode gap is provided with a gas at a specified pressure; and
  applying a rapid rise time voltage pulse across the electrodes to cause an extreme overvoltage, whereby, current flowing between the electrodes is characterized by an initial spike in current followed by a pedestal region wherein current continues to flow after the initial spike in current.

63. The method according to claim 62, wherein the overvoltage condition is caused by a peak value of the voltage pulse that exceeds at least 1.5 times a threshold voltage needed to generate plasma in the electrode gap.

64. The method according to claim 62, wherein the specified pressure ranges from approximately one atmosphere to 0.1 atmosphere.

65. The method according to claim 62, further comprising exposing an object of matter to the plasma for a specified time.

66. An object of matter processed by exposure to a plasma generated by the method according to claim 62.

67. The dielectric barrier plasma discharge device according to claim 62, wherein the plasma induces a reaction in an object of matter exposed to the plasma, and wherein the reaction includes one of chemical vapor deposition, polymerization, atomic layer deposition, and electron induced decomposition.

68. A method of sterilizing an object of matter, comprising:
  generating a plasma exhibiting a runaway electron condition, wherein the plasma is generated by producing current flowing between electrodes, and wherein the current is characterized by an initial spike in current followed by a pedestal region wherein current continues to flow after the initial spike in current; and exposing the object of matter to the plasma for a specified time, whereby the object of matter is bombarded with high energy electrons to sterilize the object.

69. An object of matter sterilized by a method comprising:

generating a plasma exhibiting a runaway electron condition, wherein the plasma is generated by producing current flowing between electrodes, and wherein the current is characterized by an initial spike in current followed by a pedestal region wherein current continues to flow after the initial spike in current; and exposing the object of matter to the plasma for a specified time, whereby the object of matter is bombarded with high energy electrons to thereby sterilize the object.

* * * * *

UNITED STATES PATENT AND TRADEMARK OFFICE
CERTIFICATE OF CORRECTION

PATENT NO. : 7,615,931 B2 Page 1 of 1
APPLICATION NO. : 11/120153
DATED : November 10, 2009
INVENTOR(S) : Hooke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this

Nineteenth Day of October, 2010

David J. Kappos
*Director of the United States Patent and Trademark Office*